United States Patent
Crawforth et al.

(10) Patent No.: US 6,872,731 B2
(45) Date of Patent: Mar. 29, 2005

(54) IMIDAZO-PYRIDINE DERIVATIVES AS LIGANDS FOR GABA RECEPTORS

(75) Inventors: James Michael Crawforth, Watton-at-Stone (GB); Simon Charles Goodacre, Benington (GB); Timothy Harrison, Great Dunmow (GB); David James Hallett, Watford (GB); Andrew Pate Owens, Huntingdon (GB); Michael Rowley, Rome (IT); Martin Richard Teall, Bishops Stortford (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 665 days.

(21) Appl. No.: 10/155,691

(22) Filed: May 23, 2002

(65) Prior Publication Data

US 2002/0188000 A1 Dec. 12, 2002

Related U.S. Application Data

(63) Continuation of application No. PCT/GB00/04451, filed on Nov. 22, 2000.

(30) Foreign Application Priority Data

Nov. 23, 1999 (GB) .......................................... 9927687.5

(51) Int. Cl.$^7$ ...................... C07D 471/04; A61K 31/435
(52) U.S. Cl. ...................................... 514/300; 546/121
(58) Field of Search ........................... 546/121; 514/300

(56) References Cited

FOREIGN PATENT DOCUMENTS

| WO | WO 99/37647 | 7/1999 |
|---|---|---|
| WO | WO 99/37648 | 7/1999 |
| WO | WO 02/02557 A2 | 1/2002 |

*Primary Examiner*—Bernard Dentz
(74) *Attorney, Agent, or Firm*—J. Eric Thies; Melvin Winokur

(57) ABSTRACT

A class of 3-phenylimidazo[1,2-a]pyridine derivatives, substituted at the meta position of the phenyl ring by an optionally substituted aryl or heteroaryl group which is directly attached or bridged by an oxygen atom or a —NH-linkage, are selective ligands for $GABA_A$ receptors, in particular having high affinity for the α2 and/or α3 subunit thereof, and are accordingly of benefit in the treatment and/or prevention of disorders of the central nervous system, including anxiety and convulsions.

11 Claims, No Drawings

IMIDAZO-PYRIDINE DERIVATIVES AS LIGANDS FOR GABA RECEPTORS

CROSS REFERENCE TO RELATED APPLICATIONS

This application is a U.S. National Phase application under 35 U.S.C. §371 of PCT Application No. PCT/GB00/04451, filed Nov. 22, 2000, which claims priority under 35 U.S.C. §119 from GB Application No. 9927687.5, filed Nov. 23, 1999.

The present invention relates to a class of substituted imidazopyridine derivatives and to their use in therapy. More particularly, this invention is concerned with imidazo[1,2-α]pyridine analogues which are substituted in the 3-position by a substituted phenyl ring. These compounds are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six α subunits, four β subunits, three γ subunits, one δ subunit, one ε subunit and two ρ subunits.

Although knowledge of the diversity of the $GABA_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional $GABA_A$ receptor expressed by transiently transfecting cDNAs into cells. As indicated above, δ, ε and ρ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, α1β2γ2, α2βγ1, α2β2/3γ2, α3βγ2/3, α4βδ, α5β3γ2/3, α6βγ2 and α6βδ. Subtype assemblies containing an α1 subunit are present in most areas of the brain and are thought to account for over 40% of $GABA_A$ receptors in the rat. Subtype assemblies containing α2 and α3 subunits respectively are thought to account for about 25% and 17% of $GABA_A$ receptors in the rat. Subtype assemblies containing an α5 subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with a β subunit and γ2. This is the most abundant $GABA_A$ receptor subtype, and is believed to represent almost half of all $GABA_A$ receptors in the brain.

Two other major populations are the α2βγ2 and α3βγ2/3 subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agonists or antagonists were known.

It is now believed that agents acting as BZ agonists at α1βγ2, α2βγ2 or α3βγ2 subtypes will possess desirable anxiolytic properties. Compounds which are modulators of the benzodiazepine binding site of the $GABA_A$ receptor by acting as BZ agonists are referred to hereinafter as "$GABA_A$ receptor agonists". The α1-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the α1 subunit. Accordingly, it is considered that $GABA_A$ receptor agonists which interact more favourably with the α2 and/or α3 subunit than with α1 will be effective in the treatment of anxiety with a reduced propensity to cause sedation. Also, agents which are antagonists or inverse agonists at α1 might be employed to reverse sedation or hypnosis caused by α1 agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as post-operative nausea and vomiting; eating disorders including anorexia nervosa and bulimia nervosa; premenstrual syndrome; muscle spasm or spasticity, e.g. in paraplegic patients; and hearing loss. Selective ligands for $GABA_A$ receptors may also be effective as pre-medication prior to anaesthesia or minor procedures such as endoscopy, including gastric endoscopy.

The present invention provides a class of imidazo-pyridine derivatives which possess desirable binding properties at various $GABA_A$ receptor subtypes. The compounds in accordance with the present invention have good affinity as ligands for the α2 and/or α3 subunit of the human GABA$_A$ receptor. The compounds of this invention may interact more favourably with the α2 and/or α3 subunit than with the α1 subunit. Desirably, the compounds of the invention will exhibit functional selectivity in terms of a selective efficacy for the α2 and/or α3 subunit relative to the α1 subunit.

The compounds of the present invention are GABA$_A$ receptor subtype ligands having a binding affinity ($K_i$) for the α2 and/or α3 subunit, as measured in the assay described hereinbelow, of 200 nM or less, typically of 100 nM or less, and ideally of 20 nM or less. The compounds in accordance with this invention may possess at least a 2-fold, suitably at least a 5-fold, and advantageously at least a 10-fold, selective affinity for the α2 and/or α3 subunit relative to the α1 subunit. However, compounds which are not selective in terms of their binding affinity for the α2 and/or α3 subunit relative to the α1 subunit are also encompassed within the scope of the present invention; such compounds will desirably exhibit functional selectivity in terms of a selective efficacy for the α2 and/or α3 subunit relative to the α1 subunit.

The present invention provides a compound of formula I, or a salt or prodrug thereof:

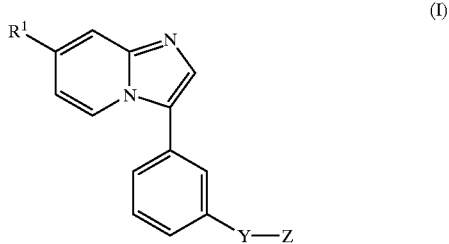

(I)

wherein
Y represents a chemical bond, an oxygen atom, or a —NH-linkage;
Z represents an optionally substituted aryl or heteroaryl group;
R$^1$ represents hydrogen, hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, —CONR$^a$R$^b$ or —CR$^a$=NOR$^b$; and
R$^a$ and R$^b$ independently represent hydrogen, hydrocarbon or a heterocyclic group.

The aryl or heteroaryl group Z in the compounds of formula I above may be unsubstituted, or substituted by one or more substituents. Typically, the group Z will be unsubstituted, or substituted by one or two substituents. Suitably, the group Z is unsubstituted or monosubstituted. Typical substituents on the group Z include halogen, cyano, nitro, amino, formyl, C$_{2-6}$ alkoxycarbonyl and —CR$^a$=NOR$^b$. Additionally, the group Z may be substituted by carboxamido.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include C$_{1-6}$ alkyl, C$_{2-6}$ alkenyl, C$_{2-6}$ alkynyl, C$_{3-7}$ cycloalkyl, C$_{3-7}$ cycloalkyl(C$_{1-6}$)alkyl, indanyl, aryl and aryl(C$_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include C$_{3-7}$ heterocycloalkyl, C$_{3-7}$ heterocycloalkyl(C$_{1-6}$)alkyl, heteroaryl and heteroaryl(C$_{1-6}$)alkyl groups.

Suitable alkyl groups include straight-chained and branched alkyl groups containing from 1 to 6 carbon atoms. Typical examples include methyl and ethyl groups, and straight-chained or branched propyl, butyl and pentyl groups. Particular alkyl groups are methyl, ethyl, n-propyl, isopropyl, isobutyl, tert-butyl and 2,2-dimethylpropyl. Derived expressions such as "C$_{1-6}$ alkoxy", "C$_{1-6}$ alkylamino" and "C$_{1-6}$ alkylsulphonyl" are to be construed accordingly.

Suitable alkenyl groups include straight-chained and branched alkenyl groups containing from 2 to 6 carbon atoms. Typical examples include vinyl, allyl and dimethylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Typical examples of C$_{3-7}$ cycloalkyl(C$_{1-6}$)alkyl groups include cyclopropylmethyl, cyclohexylmethyl and cyclohexylethyl.

Particular indanyl groups include indan-1-yl and indan-2-yl.

Particular aryl groups include phenyl and naphthyl, preferably phenyl.

Particular aryl(C$_{1-6}$)alkyl groups include benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl(C$_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, aminocarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —NR$^v$R$^w$, —NR$^v$COR$^w$, —NR$^v$CO$_2$R$^w$, —NR$^v$SO$_2$R$^w$, —CH$_2$NR$^v$SO$_2$R$^w$, —NHCONR$^v$R$^w$, —CONR$^v$R$^w$, —SO$_2$NR$^v$R$^w$ and —CH$_2$SO$_2$NR$^v$R$^w$, in which R$^v$ and R$^w$ independently represent hydrogen, $C_{1-6}$ alkyl, aryl or aryl($C_{1-6}$)alkyl.

The term "halogen" as used herein includes fluorine, chlorine, bromine and iodine, especially fluoro or chloro.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In a preferred embodiment, Y represents a chemical bond.

In another embodiment, Y represents an oxygen atom.

In a further embodiment, Y represents a —NH-linkage.

Representative values for the substituent Z include phenyl, pyridinyl, thienyl and thiazolyl, any of which groups may be optionally substituted. In a favoured embodiment, Z represents an optionally substituted phenyl group, in particular monosubstituted phenyl.

Examples of typical substituents on the group Z include chloro, methoxy, trifluoromethyl, carboxamido, cyano, nitro, amino, formyl, methoxycarbonyl and —CH=NOH. Examples of particular substituents on the group Z include chloro, carboxamido, cyano, nitro, amino, formyl, methoxycarbonyl and —CH=NOH. Examples of specific substituents on the group Z include chloro, cyano, nitro, amino, formyl, methoxycarbonyl and —CH=NOH, especially cyano.

Particular values of Z include cyanophenyl, nitrophenyl, pyridinyl, (amino)(chloro)pyridinyl, carboxamido-thienyl, cyano-thienyl, formyl-thienyl, methoxycarbonyl-thienyl, thienyl-CH=NOH and thiazolyl.

Specific values of Z include nitrophenyl, pyridinyl, (amino)(chloro)pyridinyl, cyano-thienyl, formyl-thienyl, methoxycarbonyl-thienyl, thienyl-CH=NOH and thiazolyl.

In a favoured embodiment, Z represents cyanophenyl, especially 2-cyanophenyl.

One particular value of Z is pyridinyl. Another particular value of Z is cyano-thienyl, especially 2-cyanothien-3-yl.

Typically, $R^1$ represents hydrocarbon, a heterocyclic group, halogen, cyano, trifluoromethyl, —OR$^a$, —COR$^a$, —CO$_2$R$^a$ or —CR$^a$=NOR$^b$.

Suitably, $R^1$ represents hydrocarbon, a heterocyclic group, halogen, —OR$^a$, —COR$^a$, —CO$_2$R$^a$ or —CR$^a$=NOR$^b$.

Typical values of R$^a$ include hydrogen and $C_{1-6}$ alkyl. Suitably, R$^a$ represents hydrogen or methyl.

Typical values of R$^b$ include hydrogen, $C_{1-6}$ alkyl, hydroxy($C_{1-6}$)alkyl and di($C_{1-6}$)alkylamino($C_{1-6}$)alkyl. Suitably, R$^b$ represents hydrogen, methyl, ethyl, hydroxyethyl or dimethylaminoethyl. Particular values of R$^b$ include hydrogen, hydroxyethyl and dimethylaminoethyl.

Representative values of $R^1$ include $C_{1-6}$ alkyl, halo($C_{1-6}$)alkyl, dihalo($C_{1-6}$)alkyl, hydroxy($C_{1-6}$)alkyl, heteroaryl, halogen, cyano, trifluoromethyl, $C_{1-6}$ alkoxy, formyl, $C_{2-6}$ alkylcarbonyl, $C_{2-6}$ alkoxycarbonyl and —CR$^a$=NOR$^b$, in which R$^a$ and R$^b$ are as defined above.

Illustrative values of $R^1$ include $C_{1-6}$ alkyl, hydroxy($C_{1-6}$)alkyl, heteroaryl, halogen, $C_{1-6}$ alkoxy, formyl, $C_{2-6}$ alkylcarbonyl, $C_{2-6}$ alkoxycarbonyl and —CR$^a$=NOR$^b$, in which R$^a$ and R$^b$ are as defined above.

Particular values of $R^1$ include methyl, fluoromethyl, difluoromethyl, trifluoromethyl, hydroxymethyl, hydroxyethyl, furyl, chloro, cyano, methoxy, formyl, acetyl, methoxycarbonyl and —CR$^2$=NOR$^3$, in which $R^2$ represents hydrogen or methyl, and $R^3$ represents hydrogen, hydroxyethyl or dimethylaminoethyl.

Specific values of $R^1$ include methyl, hydroxymethyl, hydroxyethyl, furyl, chloro, methoxy, formyl, acetyl, methoxycarbonyl and —CR$^2$=NOR$^3$, in which $R^2$ and $R^3$ are as defined above.

Particular values of $R^1$ include methyl, fluoromethyl, difluoromethyl and hydroxymethyl. In one embodiment, $R^1$ is $C_{1-6}$ alkyl, especially methyl.

A particular sub-class of compounds according to the invention is represented by the compounds of formula IIA, and salts and prodrugs thereof:

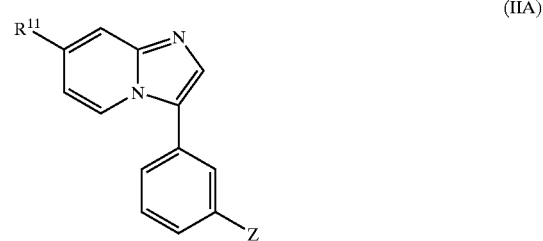

(IIA)

wherein

Z is as defined with reference to formula I above;

$R^{11}$ represents $C_{1-6}$ alkyl, halo($C_{1-6}$)alkyl, dihalo($C_{1-6}$) alkyl, hydroxy($C_{1-6}$)alkyl, heteroaryl, halogen, cyano, trifluoromethyl, $C_{1-6}$ alkoxy, formyl, $C_{2-6}$ alkylcarbonyl, $C_{2-6}$ alkoxycarbonyl or —CR$^4$=NOR$^5$;

$R^4$ represents hydrogen or $C_{1-6}$ alkyl; and $R^5$ represents hydrogen, $C_{1-6}$ alkyl, hydroxy($C_{1-6}$)alkyl or di($C_{1-6}$)alkylamino($C_{1-6}$)alkyl.

In one embodiment of the compounds of formula IIA above, Z represents an optionally substituted aryl group.

In another embodiment of the compounds of formula IIA above, Z represents an optionally substituted heteroaryl group.

Typically, $R^{11}$ represents $C_{1-6}$ alkyl, hydroxy($C_{1-6}$)alkyl, heteroaryl, halogen, $C_{1-6}$ alkoxy, formyl, $C_{2-6}$ alkylcarbonyl, $C_{2-6}$ alkoxycarbonyl or —CR$^4$=NOR$^5$, wherein $R^4$ and $R^5$ are as defined above.

Suitably, $R^4$ represents hydrogen or methyl.

Suitably, $R^5$ represents hydrogen, methyl, ethyl, hydroxyethyl or dimethylaminoethyl. Particular values of $R^5$ include hydrogen, hydroxyethyl and dimethylaminoethyl.

Where R[11] represents heteroaryl, this group is suitably furyl.

Illustrative values of R[11] include methyl, fluoromethyl, difluoromethyl, trifluoromethyl, hydroxymethyl, hydroxyethyl, furyl, chloro, cyano, methoxy, formyl, acetyl, methoxycarbonyl and —CR$^2$=NOR$^3$, in which R$^2$ and R$^3$ are as defined above.

Particular values of R[11] include methyl, hydroxymethyl, hydroxyethyl, furyl, chloro, methoxy, formyl, acetyl, methoxycarbonyl and —CR$^2$=NOR$^3$, in which R$^2$ and R$^3$ are as defined above.

Specific values of R[11] include methyl, fluoromethyl, difluoromethyl and hydroxymethyl.

One representative subset of the compounds of formula IIA above is represented by the compounds of formula IIB, and salts and prodrugs thereof:

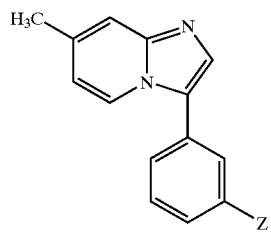

(IIB)

wherein Z is as defined with reference to formula I above.

In one embodiment of the compounds of formula IIB above, Z represents an optionally substituted aryl group.

In another embodiment of the compounds of formula IIB above, Z represents an optionally substituted heteroaryl group.

Another representative subset of the compounds of formula IIA above is represented by the compounds of formula IIC, and salts and prodrugs thereof:

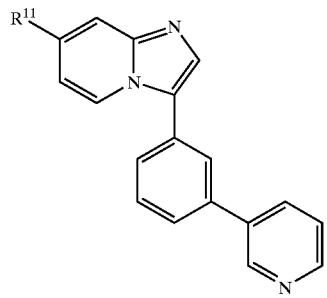

(IIC)

wherein R[11] is as defined with reference to formula IIA above.

A further representative subset of the compounds of formula IIA above is represented by the compounds of formula IID, and salts and prodrugs thereof:

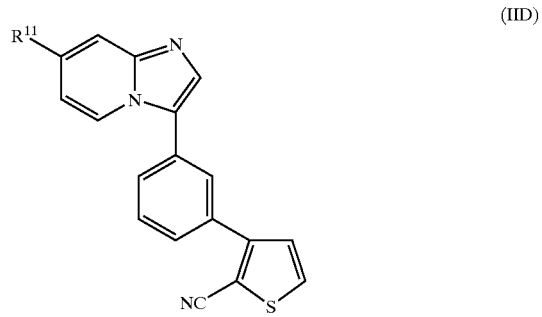

(IID)

wherein R[11] is as defined with reference to formula IIA above.

An additional representative subset of the compounds of formula IIA above is represented by the compounds of formula IIE, and salts and prodrugs thereof:

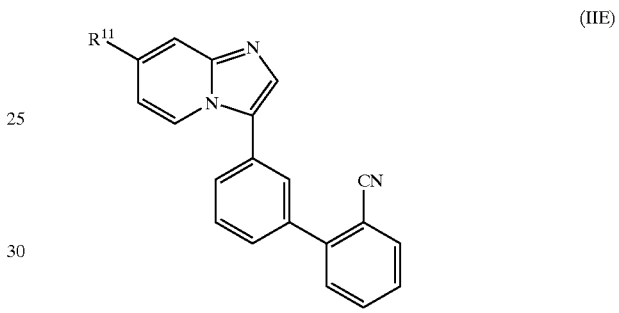

(IIE)

wherein R[11] is as defined with reference to formula IIA above.

Specific compounds within the scope of the present invention include:

3-[3-(7-methylimidazo[1,2-α]pyridin-3-yl)phenyl] thiophene-2-carbonitrile;
3-[3-(7-methylimidazo[1,2-α]pyridin-3-yl)phenyl] thiophene-2-carboxaldehyde;
3-[3-(7-methylimidazo[1,2-α]pyridin-3-yl)phenyl] thiophene-2-carboxylic acid methyl ester;
5-[3-(7-methylimidazo[1,2-α]pyridin-3-yl)phenyl] thiophene-2-carboxaldehyde oxime;
7-methyl-3-[3-(thiazol-4-yl)phenyl]imidazo[1,2-α] pyridine;
7-methyl-3-[3-(thiazol-2-yl)phenyl]imidazo[1,2-α] pyridine;
7-methyl-3-[3-(pyridin-4-yl)phenyl]imidazo[1,2-α] pyridine;
6-chloro-4-[3-(7-methylimidazo[1,2-α]pyridin-3-yl)phenyl] pyridin-3-ylamine;
7-methyl-3-[3-(pyridin-2-yloxy)phenyl]imidazo[1,2-α] pyridine;
N-[3-(7-methylimidazo[1,2-α]pyridin-3-yl)phenyl]-N-(2-nitrophenyl)amine;
3-[3-(pyridin-3-yl)phenyl]imidazo[1,2-α]pyridine-7-carboxylic acid methyl ester;
3-[3-(pyridin-3-yl)phenyl]imidazo[1,2-α]pyridin-7-ylmethanol;
3-[3-(pyridin-3-yl)phenyl]imidazo[1,2-α]pyridine-7-carboxaldehyde;
3-[3-(pyridin-3-yl)phenyl]imidazo[1,2-α]pyridine-7-carboxaldehyde oxime;
3-[3-(pyridin-3-yl)phenyl]imidazo[1,2-α]pyridine-7-carboxaldehyde O-(2-hydroxyethyl)oxime;

3-[3-(pyridin-3-yl)phenyl]imidazo[1,2-α]pyridine-7-
carboxaldehyde O-(2-dimethylaminoethyl)oxime;
1-[3-(3-(pyridin-3-yl)phenyl)imidazo[1,2-α]pyridin-7-yl]
ethanol;
1-[3-(3-(pyridin-3-yl)phenyl)imidazo[1,2-α]pyridin-7-yl]
ethanone;
1-[3-(3-(pyridin-3-yl)phenyl)imidazo[1,2-α]pyridin-7-yl]
ethanone oxime;
7-chloro-3-[3-(pyridin-3-yl)phenyl]imidazo[1,2-α]pyridine;
7-(furan-3-yl)-3-[3-(pyridin-3-yl)phenyl]imidazo[1,2-α]
pyridine;
7-methoxy-3-[3-(pyridin-3-yl)phenyl]imidazo[1,2-α]
pyridine;
3'-(7-methylimidazo[1,2-α]pyridin-3-yl)biphenyl-2-
carbonitrile;
3-[3-(7-methylimidazo[1,2-α]pyridin-3-yl)phenyl]
thiophene-2-carboxamide;
3-[3-(2-cyanothien-3-yl)phenyl]imidazo[1,2-α]pyridine-7-
carboxylic acid methyl ester;
3-[3-(7-formylimidazo[1,2-α]pyridin-3-yl)phenyl]
thiophene-2-carbonitrile;
3-[3-(7-hydroxyiminomethylimidazo[1,2-α]pyridin-3-yl)
phenyl]thiophene-2-carbonitrile;
3-[3-(7-(2-hydroxyethoxy)iminomethylimidazo[1,2-α]
pyridin-3-yl)phenyl]thiophene-2-carbonitrile;
3-[3-(7-(2-dimethylaminoethoxy)iminomethylimidazo[1,2-
α]pyridin-3-yl)phenyl]thiophene -2-carbonitrile;
3'-(7-formylimidazo[1,2-α]pyridin-3-yl)biphenyl-2-
carbonitrile;
3'-(7-hydroxyiminomethylimidazo[1,2-α]pyridin-3-yl)
biphenyl-2-carbonitrile;
3'-(7-difluoromethylimidazo[1,2-α]pyridin-3-yl)biphenyl-
2-carbonitrile;
3'-(7-hydroxymethylimidazo[1,2-α]pyridin-3-yl)biphenyl-
2-carbonitrile;
3'-(7-fluoromethylimidazo[1,2-α]pyridin-3-yl)biphenyl-2-
carbonitrile;
and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof or a prodrug thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof or a prodrug thereof.

The binding affinity ($K_i$) of the compounds according to the present invention for the α3 subunit of the human $GABA_A$ receptor is conveniently as measured in the assay described hereinbelow. The α3 subunit binding affinity ($K_i$) of the compounds of the invention is ideally 50 nM or less, preferably 10 nM or less, and more preferably 5 nM or less.

The compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk⁻ fibroblast cells.

The compounds according to the present invention exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention in which Y represents a chemical bond may be prepared by a process which comprises reacting a compound of formula III with a compound of formula IV:

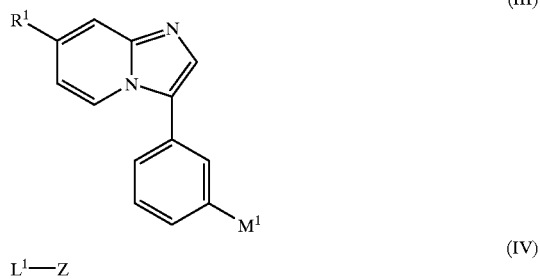

wherein Z and $R^1$ are as defined above, $L^1$ represents a suitable leaving group, and $M^1$ represents a boronic acid moiety $-B(OH)_2$ or a cyclic ester thereof formed with an organic diol, e.g. pinacol; in the presence of a transition metal catalyst.

The leaving group $L^1$ is typically a halogen atom, e.g. bromo.

The transition metal catalyst of use in the reaction between compounds III and IV is suitably tetrakis(triphenylphosphine)pallidum(0). The reaction is conveniently carried out at an elevated temperature in an inert solvent such as 1,2-dimethoxyethane, advantageously in the presence of a base such as cesium carbonate.

In another procedure, the compounds according to the present invention in which Y represents an oxygen atom may be prepared by a process which comprises reacting a compound of formula IV as defined above with a compound of formula V:

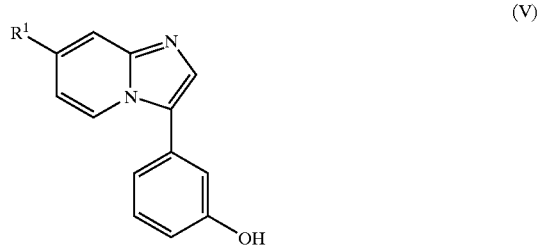

wherein $R^1$ is as defined above.

The reaction is conveniently carried out under basic conditions, e.g. using sodium hydride in a solvent such as N,N-dimethylformamide, typically at an elevated temperature which may be in the region of 120° C.

In a further procedure, the compounds according to the present invention in which Y represents a —NH-linkage may be prepared by a process which comprises reacting a compound of formula IV as defined above with a compound of formula VI:

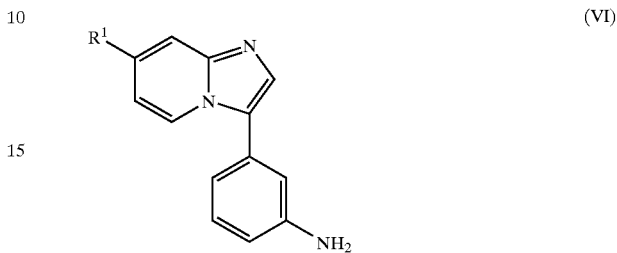

wherein $R^1$ is as defined above.

In relation to the reaction between compounds IV and VI, the leaving group $L^1$ in the compounds of formula IV may suitably represent fluoro.

The reaction between compounds IV and VI is conveniently carried out by heating the reactants, typically at a temperature in the region of 120° C., in a solvent such as N,N-dimethylformamide.

Where $M^1$ in the intermediates of formula III above represents a cyclic ester of a boronic acid moiety $-B(OH)_2$ formed with pinacol, the relevant compound III may be prepared by reacting bis(pinacolato)-diboron with a compound of formula VII:

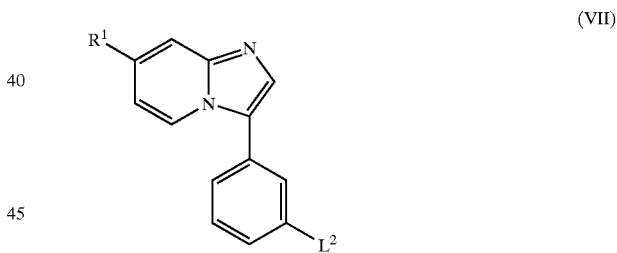

wherein $R^1$ is as defined above, and $L^2$ represents a suitable leaving group; in the presence of a transition metal catalyst.

The leaving group $L^2$ is typically trifluoromethanesulphonyloxy.

The transition metal catalyst of use in the reaction between bis(pinacolato)diboron and compound VII is suitably dichloro[1,1'-bis(diphenylphosphino)ferrocenelpalladium(II). The reaction is conveniently carried out at an elevated temperature in a solvent such as 1,4-dioxane, typically in the presence of 1,1'-bis(diphenylphosphino)-ferrocene and potassium acetate.

Where $L^2$ in the intermediates of formula VII above represents trifluoromethanesulphonyloxy, the relevant compound VII may be prepared by reacting the appropriate compound of formula V as defined above with trifluoromethanesulphonic anhydride, typically in the presence of pyridine.

The intermediates of formula V above may suitably be prepared from the appropriate methoxy-substituted precursor of formula VIII:

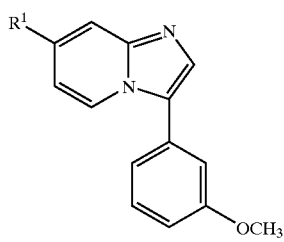
(VIII)

wherein $R^1$ is as defined above; by treatment with hydrogen bromide, typically in acetic acid at reflux.

The intermediates of formula VI and VIII above may be prepared by reacting a compound of formula IX with the appropriate compound of formula X:

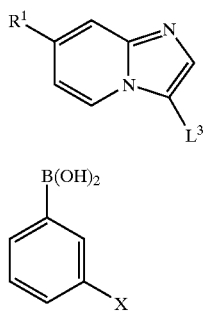
(IX)

(X)

wherein $R^1$ is as defined above, X represents amino or methoxy, and $L^3$ represents a suitable leaving group; in the presence of a transition metal catalyst.

The leaving group $L^3$ is typically a halogen atom, e.g. bromo.

The transition metal catalyst of use in the reaction between compounds IX and X is suitably tetrakis(triphenylphosphine)pallidum(0). The reaction is conveniently carried out at an elevated temperature in an inert solvent such as 1,2-dimethoxyethane, advantageously in the presence of a base such as sodium carbonate.

In a still further procedure, the compounds according to the present invention may be prepared by a process which comprises reacting a compound of formula IX as defined above with a compound of formula XI:

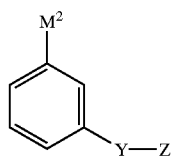
(XI)

wherein Y and Z are as defined above, and $M^2$ represents $Sn(Alk)_3$ in which Alk represents $C_{1-6}$ alkyl, typically n-butyl, or $M^2$ represents a boronic acid moiety $-B(OH)_2$ or a cyclic ester thereof formed with an organic diol, e.g. pinacol; in the presence of a transition metal catalyst.

The transition metal catalyst of use in the the reaction between compounds IX and XI is suitably tetrakis(triphenylphosphine)pallidum(0). Where $M^2$ represents $Sn(Alk)_3$, the reaction is conveniently carried out at an elevated temperature in an inert solvent such as N,N-dimethylformamide, typically in the presence of lithium chloride and copper(I) iodide. Where $M^2$ represents a boronic acid moiety or a cyclic ester thereof formed with an organic diol, e.g. pinacol, the reaction is conveniently carried out at an elevated temperature, e.g. a temperature in the region of 80° C., in a solvent such as 1,2-dimethoxyethane or N,N-dimethylacetamide, typically in the presence of sodium carbonate or potassium phosphate.

Where $L^3$ in the intermediates of formula IX above represents bromo, this compound may be prepared by bromination of the corresponding compound of formula XII:

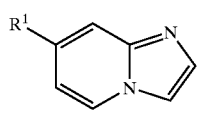
(XII)

wherein $R^1$ is as defined above; typically by treatment with bromine in methanol, in the presence of sodium acetate and optionally also potassium bromide.

The intermediates of formula XII may be prepared by reacting chloroacetaldehyde with the requisite compound of formula XIII:

(XIII)
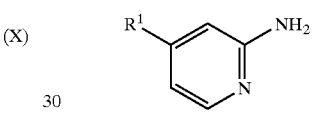

wherein $R^1$ is as defined above.

The reaction is conveniently carried out by heating the reactants under basic conditions in a suitable solvent, e.g. sodium hydrogencarbonate in a lower alkanol such as methanol or ethanol at the reflux temperature of the solvent.

In a yet further procedure, the compounds according to the present invention wherein $R^1$ represents an aryl or heteroaryl moiety may be prepared by a process which comprises reacting a compound of formula XIV with a compound of formula XV:

(XIV)

(XV)
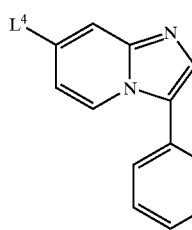

wherein Y and Z are as defined above, $R^{1a}$ represents an aryl or heteroaryl moiety, and $L^4$ represents a suitable leaving group; in the presence of a transition metal catalyst.

The leaving group $L^4$ is typically a halogen atom, e.g. chloro.

The transition metal catalyst of use in the reaction between compounds XIV and XV is suitably tris(dibenzylideneacetone)pallidum(0), in which case the reaction is conveniently effected at an elevated temperature in a solvent such as 1,4-dioxane, typically in the presence of tri-tert-butylphosphine and cesium carbonate.

Where $L^4$ in the compounds of formula XV above represents a halogen atom, these compounds correspond to compounds of formula I as defined above wherein $R^1$ represents halogen, and they may therefore be prepared by any of the methods described above for the preparation of the compounds according to the invention.

Where they are not commercially available, the starting materials of formula IV, X, XI, XIII and XIV may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I wherein $R^1$ represents $C_{1-6}$ alkoxycarbonyl initially obtained may be reduced with a reducing agent, typically lithium aluminium hydride or sodium borohydride, to the corresponding compound of formula I wherein $R^1$ represents hydroxymethyl. The latter compound may then be oxidised to the corresponding compound of formula I wherein $R^1$ represents formyl by treatment with manganese dioxide. A compound of formula I wherein $R^1$ represents formyl may be condensed with a hydroxylamine derivative of formula $H_2N$—$OR^b$ to provide a compound of formula I wherein $R^1$ represents —CH=NOR$^b$. Alternatively, the compound of formula I wherein $R^1$ represents formyl may be reacted with a Grignard reagent of formula $R^a$MgBr to afford a compound of formula I wherein $R^1$ represents —CH(OH)R$^a$, and this compound may in turn be oxidised using manganese dioxide to the corresponding compound of formula I wherein $R^1$ represents —COR$^a$. The latter compound may then be condensed with a hydroxylamine derivative of formula $H_2N$—$OR^b$ to provide a compound of formula I wherein $R^1$ represents —CR$^a$=NOR$^b$. A compound of formula I wherein $R^1$ represents hydroxymethyl or formyl may be treated with (diethylamino)sulfur trifluoride to afford a compound of formula I wherein $R^1$ represents fluoromethyl or difluoromethyl respectively. Furthermore, a compound of formula I wherein $R^1$ represents —CH=NOH may be converted into the corresponding compound of formula I wherein $R^1$ represents cyano by treatment with 1,1'-carbonyldiimidazole in the presence of an organic base such as triethylamine.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human $GABA_A$ receptors containing the α2 or α3 subunit stably expressed in Ltk$^-$ cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [3H]-flumazenil from the α2 and/or α3 subunit of the human $GABA_A$ receptor of 100 nM or less.

EXAMPLE 1

3-[3-(7-Methylimidazo[1,2-α]pyridin-3-yl)phenyl]thiophene-2-carbonitrile

A solution of 2-amino-4-methylpyridine (21.6 g, 0.2 mol) in ethanol (300 ml) was treated with sodium hydrogencarbonate (33.6 g, 0.4 mol) then with chloroacetaldehyde (42.4 ml of a 45 wt % solution in water, 0.3 mol) and this mixture was heated at reflux for 16 hours. The reaction was cooled then pre-adsorbed directly on to silica (200 g). Purification by dry flash chromatography, eluting with dichloromethane/methanol/conc. ammonia (95:4.5:0.5) gave 7-methylimidazo[1,2-α]pyridine as an oil (26.4 g, 100%) which crystallised on standing. ¹H NMR (400 MHz, CDCl₃) δ$_H$ 2.39 (3H, s), 6.62 (1H, d, J 7), 7.37 (1H, s), 7.49 (1H, s), 7.55 (1H, s), 8.00 (1H, d, J 7); m/z (ES⁺) 132 (M⁺+H).

A cooled (−10° C.) suspension of 7-methylimidazo[1,2-α]pyridine (26 g, 0.2 mol) and sodium acetate (24.3 g, 0.3 mol) in methanol (150 ml) was treated with bromine (ca. 10 ml, 0.2 mol) added dropwise until the first permanent colour change occurred. Stirring was continued for a further 20 minutes before the reaction was poured into saturated aqueous sodium hydrogencarbonate (2 l). The resulting solid was filtered, washed with water and dried. Trituration with 5% ether in isohexane furnished 3-bromo-7-methylimidazo[1,2-α]pyridine as a red-brown powder (41.5 g, 100%). ¹H NMR (360 MHz, CDCl₃) δ$_H$ 2.43 (3H, s), 6.76 (1H, d, J 7), 7.37 (1H, s), 7.53 (1H, s), 7.55 (1H, s), 8.00 (1H, d, J 7); m/z (ES⁺) 210/212 (M⁺+H).

A mixture of 3-bromo-7-methylimidazo[1,2-α]pyridine (18.0 g, 86 mmol) and 3-methoxyphenylboronic acid (17.0 g, 112 mmol) in 1,2-dimethoxyethane (250 ml) and sodium carbonate (120 ml of a 2M aqueous solution) was degassed for 25 minutes. Tetrakis(triphenylphosphine)pallidum(0) (500 mg, 0.4 mmol) was then added and the mixture heated at reflux for 17 hours. After cooling to ambient temperature the reaction was poured into water (400 ml), extracted with ethyl acetate (3×400 ml) and the combined organics dried over anhydrous magnesium sulphate. Filtration and evaporation to dryness afforded 3-(3-methoxyphenyl)-7-methylimidazo[1,2-α]pyridine as a colourless oil (19 g, 93%). ¹H NMR (360 MHz, CDC₃) δ$_H$ 2.40 (3H, s), 3.84 (3H, s), 6.63–6.65 (1H, m), 6.91–6.95 (1H, m), 7.05–7.07 (1H, m), 7.10–7.12 (1H, m), 7.30–7.38 (1H, m), 7.42 (1H, s), 7.66 (1H, s), 8.22 (1H, d, J 7); m/z (ES⁺) 239 (M⁺+H).

A solution of 3-(3-methoxyphenyl)-7-methylimidazo[1,2-α]pyridine (19 g, 80 mmol) in hydrogen bromide (160 ml of a 45% w/v solution in acetic acid) was heated at reflux for 18 hours. The cooled reaction was poured into sodium hydroxide solution (800 ml of a 4M aqueous solution), the pH adjusted to 7 with acetic acid and the resulting cream-coloured solid filtered and dried under vacuum at 60° C. to yield 3-(7-methylimidazo[1,2-α]pyridin-3-yl)phenol (18 g, 95%). ¹H NMR (400 MHz, CDCl₃) δ$_H$ 6.79–6.83 (2H, m), 6.96–7.01 (2H, m), 7.30–7.33 (1H, m), 7.41 (1H, s), 7.62 (1H, s), 8.42 (1H, d, J 7); m/z (ES⁺) 225 (M⁺+H).

To a cooled (−78° C.) suspension of 3-(7-methylimidazo[1,2-α]pyridin-3-yl)phenol (8.0 g, 35.7 mmol) in dry dichloromethane (80 ml) was added dry pyridine (4.2 ml, 51.9 mmol) and the mixture stirred for 15 minutes. Trifluoromethanesulfonic anhydride (4.6 ml, 43.2 mmol) was added slowly and the reaction mixture stirred for 1 hour then allowed to warm to ambient temperature for a further hour before pouring into water (100 ml). The organic phase was separated, washed with water (100 ml), brine (100 ml), water (100 ml), dried over anhydrous magnesium sulphate and concentrated in vacuo. The residue was purified by flash chromatography eluting with dichloromethane on a gradient of methanol from 3% to 5% to give trifluoromethanesulfonic acid 3-(7-methylimidazo[1,2-α]pyridin-3-yl)phenyl ester as a cream solid (7.6 g, 60%). ¹H NMR (400 MHz, CDCl₃) δ$_H$ 6.71–6.74 (1H, m), 7.26–7.37 (2H, m), 7.45–7.47 (2H, m), 7.57–7.59 (2H, m), 7.67 (1H, s), 8.20 (1H, d, J 7); m/z (ES⁺) 357 (M⁺+H).

Bis(pinacolato)diboron (5.8 g, 22.8 mmol), potassium acetate (5.6 g, 57.1 mmol) and trifluoromethanesulfonic acid 3-(7-methylimidazo[1,2-α]pyridin-3-yl)phenyl ester (6.8 g, 19.0 mmol) were combined and purged with nitrogen. Anhydrous 1,4-dioxane (50 ml), dichloro[1,1'-bis(diphenylphosphino)ferrocene]palladium(II) (470 mg, 0.57 mmol) and 1,1'-bis(diphenylphosphino)ferrocene (315 mg, 0.57 mmol) were added and the mixture heated at 80° C. for 18 hours. The cooled reaction was filtered through Celite®, concentrated, and dried at 60° C. under vacuum to yield 7-methyl-3-[3-(4,4,5,5-tetramethyl-[1,3,2,]dioxaborolan-2-yl)phenyl]imidazo[1,2-α]pyridine as a dark brown solid (5.7 g, 90%). ¹H NMR (400 MHz, CDCl₃) δ$_H$ 1.36 (12H, s), 2.45 (3H, s), 6.65 (1H, d, J 7), 7.46–7.52 (1H, m), 7.61–7.64 (1H, m), 7.84 (1H, d, J 7), 7.98 (1H, s), 8.20 (1H, d, J 7); m/z (ES⁺) 335 (M⁺+H).

A mixture of 7-methyl-3-[3-(4,4,5,5-tetramethyl-[1,3,2] dioxaborolan-2-yl)phenyl]imidazo[1,2-α]pyridine (350 mg, 1.0 mmol) and 3-bromo-2-cyanothiophene (200 mg, 1.0 mmol) in 1,2-dimethoxyethane (10 ml) and caesium carbonate (5 ml of a 2M solution) was degassed for 15 minutes. Tetrakis(triphenylphosphine)palladium(0) (125 mg, 0.1 mmol) was then added and the mixture heated at reflux for 20 hours, poured into water (50 ml) and extracted with ethyl acetate (2×25 ml). The combined organic phases were dried over anhydrous magnesium sulphate, filtered and concentrated in vacuo. Purification by flash chromatography eluting with 3% methanol in dichloromethane gave the title compound as a colourless oil (180 mg, 57%). Oxalate salt, white powder, m.p. 193–195° C. (Found C, 62.07; H, 3.66; N, 10.19. C₁₉H₁₃N₃S.C₂H₂O₄ requires C, 62.21; H, 3.73; N, 10.36). ¹H NMR (360 MHz, d₆-DMSO) δ$_H$ 2.42 (3H, s), 6.91–6.93 (1H, m), 7.53 (1H, s), 7.68–7.82 (6H, m), 7.89 (1H, s), 8.01 (1H, s), 8.18 (1H, d, J 5), 8.63 (1H, d, J 7); m/z (ES⁺) 316 (M⁺+H).

The following compounds were prepared in a similar manner to that described for Example 1 starting from 7-methyl-3-[3-(4,4,5,5-tetramethyl-[1,3,2]dioxaborolan-2-yl)phenyl]imidazo[1,2-α]pyridine and the appropriate aryl or heteroaryl halide:

EXAMPLE 2

3-[3-(7-Methylimidazo[1,2-α]pyridin-3-yl)phenyl] thiophene-2-carboxaldehyde m/z (ES⁺) 319 (M⁺+H).

EXAMPLE 3

3-[3-(7-Methylimidazo[1,2-α]pyridin-3-yl)phenyl] thiophene-2-carboxylic acid methyl ester m/z (ES⁺) 349 (M⁺+H).

EXAMPLE 4

5-[3-(7-Methylimidazo[1,2-α]pyridin-3-yl)phenyl] thiophene-2-carboxaldehyde oxime m/z (ES⁺) 334 (M⁺+H).

EXAMPLE 5

7-Methyl-3-[3-(thiazol-4-yl)phenyl]imidazo[1,2-α] pyridine m/z (ES⁺) 292 (M⁺+H).

EXAMPLE 6

7-Methyl-3-[3-(thiazol-2-yl)phenyl]imidazo[1,2-α] pyridine m/z (ES⁺) 292 (M⁺+H).

EXAMPLE 7

7-Methyl-3-[3-(pyridin-4-yl)phenyl]imidazo[1,2-α]pyridine m/z (ES$^+$) 286 (M$^+$+H).

EXAMPLE 8

6-Chloro-4-[3-(7-methylimidazo[1,2-α]pyridin-3-yl)phenyl]pyridin-3-ylamine m/z (ES$^+$) 335 (M$^+$+H).

EXAMPLE 9

7-Methyl-3-[3-(pyridin-2-yloxy)phenyl]imidazo[1,2-α]pyridine 3-(7-Methylimidazo[1,2-α]pyridin-3-yl)phenol (310 mg, 1.4 mmol) in anhydrous N,N-dimethylformamide (5 ml) was treated with sodium hydride (60% dispersion in mineral oil, 70 mg, 1.75 mmol) and then stirred at ambient temperature for 30 minutes. 2-Bromopyridine (0.16 ml, 1.67 mmol) was added and the reaction mixture heated at 120° C. for 4 days, poured into water (25 ml) and extracted with ethyl acetate (2×30 ml). The combined organic phases were washed with water (3×20 ml), dried over anhydrous magnesium sulphate and concentrated in vacuo. Purification by preparative TLC gave the title compound as a colourless oil (100 mg, 24%). $^1$H NMR (400 MHz, CDCl$_3$) $\delta_H$ 2.64 (3H, s), 7.08–7.10 (1H, m), 7.14–7.17 (1H, m), 7.33–7.37 (2H, m), 7.50–7.55 (2H, m), 7.66–7.70 (1H, m), 7.78 (1H, s), 7.85–7.90 (1H, m), 8.07 (1H, s), 8.15–8.16 (1H, m), 8.65 (1H, d, J 7); m/z (ES$^+$) 302 (M$^+$+H).

EXAMPLE 10

N-[3-(7-Methylimidazo[1,2-α]pyridin-3-yl)phenyl]-N-(2-nitrophenyl)amine

3-Bromo-7-methylimidazo[1,2-α]pyridine (4.2 g, 20.0 mmol) and 3-aminophenylboronic acid (4.0 g, 25.8 mmol) were suspended in 1,2-dimethoxyethane (80 ml) and sodium carbonate (40 ml of a 2M solution) and the resulting solution degassed for 25 minutes. Tetrakis(triphenylphosphine)palladium(0) (250 mg, 0.2 mmol) was added and the mixture heated at reflux for 17 hours. The cooled reaction mixture was poured into water (150 ml), extracted with ethyl acetate (3×70 ml) and the combined organics dried over anhydrous magnesium sulphate. The solution was filtered and concentrated in vacuo to yield 3-(3-aminophenyl)-7-methylimidazo[1,2-α]pyridine as a colourless oil (4.5 g, 100%) which was used without further purification. $^1$H NMR (400 MHz, CDCl$_3$) $\delta_H$ 2.38 (3H, s), 3.58 (2H, br s), 6.60 (1H, d, J 7), 6.70 (1H, d, J 8), 6.81 (1H, s), 6.91 (1H, d, J8), 7.24–7.28 (1H, m), 7.39 (1H, s), 7.57 (1H, s), 8.23 (1H, d, J 7); m/z (ES$^+$) 224 (M$^+$+H).

3-(3-Aminophenyl)-7-methylimidazo[1,2-α]pyridine (1.0 g, 4.5 mmol) and 1-fluoro-2-nitrobenzene (0.55 ml, 5.2 mmol) were dissolved in anhydrous N,N-dimethylformamide (10 ml) and heated at 120° C. for 2 days. The cooled reaction mixture was poured into water (25 ml), extracted with ethyl acetate (2×20 ml) and the combined organic phases dried over anhydrous magnesium sulphate and concentrated in vacuo. Purification by flash chromatography eluting with 5% methanol in dichloromethane gave the title compound as an orange oil (160 mg, 10%). $^1$H NMR (400 MHz, d$_4$-methanol) $\delta_H$ 2.61 (3H, s), 6.89–6.93 (1H, m), 7.33–7.35 (1H, m), 7.40–7.42 (1H, m), 7.47–7.52 (2H, m), 7.55–7.57 (1H, m), 7.62–7.69 (2H, m), 7.74 (1H, s), 8.06 (1H, s), 8.24 (1H, d, J 7), 8.67 (1H, d, J 8); m/z (ES$^+$) 345 (M$^+$+H).

EXAMPLE 11

3-[3-(Pyridin-3-yl)phenyl]imidazo[1,2-α]pyridine-7-carboxylic acid methyl ester

Part A

3-[3-(Tri-n-butylstannanyl)phenyl]pyridine

A mixture of 1,3-dibromobenzene (105.0 g, 0.45 mol), diethyl(3-pyridyl)borane (30.0 g, 0.204 mol) and tetrabutylammonium hydroxide (2 ml of a 40 wt % solution in water) in 1,2-dimethoxyethane (200 ml) and sodium carbonate (100 ml of a 2M solution) was degassed with nitrogen for 15 min before addition of tetrakis(triphenylphosphine)palladium(0) (4.5 g, 3.9 mmol). The mixture was heated at 80° C. for 18 h, cooled to room temperature, diluted with ethyl acetate and extracted with 1M hydrochloric acid (4×250 ml). The combined aqueous phases were made basic with solid sodium hydroxide and then extracted with diethyl ether. The organic layer was washed with water, brine, dried over sodium sulphate and concentrated to give a yellow oil. Purification by silica gel chromatography eluting with isohexane on a gradient of diethyl ether (10% to 50%) gave 3-(3-bromophenyl)pyridine (33.5 g, 70%) as a colourless oil. $^1$H NMR (400 MHz, CDCl$_3$) $\delta_H$ 7.28–7.40 (2H, m), 7.48–7.57 (2H, m), 7.73 (1H, t, J 2), 7.82–7.87 (1H, m), 8.62 (1H, s), 8.80 (1H, s).

A cooled (−78° C.) solution of 3-(3-bromophenyl)pyridine (7.50 g, 32 mmol) in tetrahydrofuran (120 ml) was treated with a cooled (−78° C.) solution of tert-butyllithium (41 ml of a 1.7M solution in hexanes, 70 mmol). After 5 minutes tri-n-butyltin chloride (9.6 ml) was added and the mixture was allowed to warm to room temperature over 1 h. Methanol (7.5 ml) and triethylamine (7.5 ml) were added and the solvent evaporated. The residue was partitioned between ethyl acetate and saturated sodium hydrogencarbonate solution, the organics washed with brine, dried and evaporated to give a yellow oil. This oil was purified by silica gel flash column chromatography eluting with isohexane/ethyl acetate/triethylamine (99:1:0.5 through to 80:20:0.5) to afford 3-[3-(tri-n-butylstannanyl)phenyl]pyridine (11.7 g, 82%) as a colourless oil. $^1$H NMR (360 MHz, CDCl$_3$) $\delta_H$ 0.86–0.93 (3H, m), 1.06–1.12 (2H, m), 1.28–1.40 (2H, m), 1.54–1.56 (2H, m), 7.34–7.39 (2H, m), 7.48–7.52 (2H, m), 7.62–7.65 (1H, m), 7.83–7.88 (1H, m), 8.57–8.60 (1H, m), 8.85 (1H, s).

Part B

A suspension of 2,4-pyridinedicarboxylic acid monohydrate (92.6 g, 0.5 mol) in acetic acid (700 ml) was treated with hydrogen peroxide (300 ml of a 35 wt % solution in water) and then heated at reflux for 16 h. The mixture was allowed to cool to 80° C., water (200 ml) was added and the mixture refrigerated at 4° C. for 16 h. The resulting solid was collected by filtration, washed with cold water (3×100 ml) and dried to give 2,4-pyridinedicarboxylic acid N-oxide (91.5 g, 91%) as a white crystalline solid. $^1$H NMR (360 MHz, d$_6$-DMSO) $\delta_H$ 8.17 (1H, dd, J 3 and 7), 8.51 (1H, d, J 3), 8.76 (1H, d, J 7).

A mixture of acetic anhydride (16.8 g, 0.164 mol), triethylamine (33.1 g, 0.327 mol) and acetonitrile (107.4 g, 2.61 mol) was heated to 45° C. before adding 2,4-pyridinedicarboxylic acid N-oxide (22.0 g, 0.12 mol) as a single portion. Once the evolution of carbon dioxide had subsided the resulting dark mixture was left to stir for 1 hour at 45° C. The solvent was evaporated, the residue dissolved in 10% potassium hydroxide solution (200 ml) and then heated at reflux for 16 h. The mixture was cooled to 0° C., neutralised with concentrated hydrochloric acid and the aqueous slurry evaporated to dryness. The residue was suspended in methanol (200 ml), hydrogen chloride gas was bubbled through this suspension for 5 minutes and the mixture was then heated at reflux for 16 h. The reaction was cooled, the solids removed by filtration and the filtrate concentrated to give a black oil. The residue was mixed with water (600 ml) and carefully made basic with solid sodium hydrogencarbonate. The aqueous was extracted with ethyl acetate (2×500 ml), the organics combined, washed with brine, dried over sodium sulphate containing 3 g decolourising charcoal, filtered and evaporated to give 2-aminopyridin-4-ylcarboxylic acid methyl ester (13.0 g) as a tan powder contaminated with ca. 20% 2-hydroxypyridin-4-ylcarboxylic acid methyl ester. Used without further purification. A small sample was purified by silica gel chromatography eluting with dichloromethane/methanol/conc. ammonia (95:4.5:0.5) giving the aminopyridine as a pale yellow solid. $^1$H NMR (400 MHz, d$_6$-DMSO) $\delta_H$ 2.50 (3H, s), 8.49 (1H, dd, J 3 and 7), 8.65 (1H, d, J 3), 8.80 (1H, d, J 7).

A solution of crude 2-aminopyridin-4-ylcarboxylic acid methyl ester (13.0 g) in methanol (150 ml) was treated with sodium hydrogencarbonate (14.3 g, 0.171 mol) and chloroacetaldehyde (8 ml of a 45 wt % solution in water) then heated at reflux for 16 h. The reaction was cooled and pre-adsorbed directly on to silica gel. Purification by flash chromatography eluting with dichloromethane (+1% conc. ammonia) on a gradient of methanol (1%–4%) gave a solid which was triturated with 5% ether in isohexane to afford imidazo[1,2-α]pyridine-7-carboxylic acid methyl ester (8.0 g, 38% from pyridine N-oxide) as a tan solid. $^1$H NMR (400 MHz, CDCl$_3$) $\delta_H$ 3.97 (3H, s), 7.37–7.43 (2H, m), 7.70 (1H, s), 7.80 (1H, s), 8.18 (1H, dd, J 1 and 7), 8.38 (1H, s).

Imidazo[1,2-α]pyridine-7-carboxylic acid methyl ester (0.53 g, 3.0 mmol) and sodium acetate (0.30 g, 3.6 mmol) were dissolved in a saturated solution of potassium bromide in methanol (5 ml) and cooled to 0° C. before dropwise addition of bromine (0.50 g, 3.2 mmol) over 5 min. The mixture was allowed to stir for 15 minutes before adding saturated sodium sulphite solution (1 ml). The reaction was evaporated to dryness and the residue partitioned between ethyl acetate and 10% sodium sulphate solution. The organics were washed with water, brine, dried over sodium sulphate and concentrated to give a yellow oil. This oil was purified by flash column chromatography on silica eluting with dichloromethane/methanol/conc. ammonia (gradient 99:1:0.1 through to 96:4:0.4) to give 3-bromo-imidazo[1,2-α]pyridine-7-carboxylic acid methyl ester (0.63 g, 83%) as a white solid. $^1$H NMR (400 MHz, CDCl$_3$) $\delta_H$ 3.98 (3H, s), 7.55 (1H, dd, J 2 and 7), 7.79 (1H, s), 8.16 (1H, dd, J 2 and 7), 8.36 (1H, d, J 2).

3-Bromoimidazo[1,2-α]pyridine-7-carboxylic acid methyl ester (10.8 g, 0.044 mol), 3-[3-(tri-n-butylstannanyl)phenyl]pyridine (20.1 g, 0.056 mol), lithium chloride (17.95 g, 0.42 mol) and copper(I) iodide (0.75 g, 4.2 mmol) were suspended in N,N-dimethylformamide (100 ml) and degassed with nitrogen for 30 min before addition of tetrakis(triphenylphosphine)pallidum(0) (2.44 g, 2.12 mmol). The mixture was heated at 80° C. for 16 h, cooled to room temperature, dissolved in 50% methanol in dichloromethane (300 ml) and pre-adsorbed onto silica gel. Purification by silica gel chromatography eluting with dichloromethane/methanol/conc. ammonia (gradient 99:1:0.1 through to 97:3:0.3) gave the title compound (8.80 g, 63%) as pale yellow needles. $^1$H NMR (360 MHz, d$_6$-DMSO) $\delta_H$ 3.98 (3H, s), 7.38–7.47 (2H, m), 7.60–7.70 (3H, m), 7.77 (1H, t, J 1), 7.90–7.95 (2H, m), 8.38 (1H, dd, J 7 and 1), 8.43 (1H, d, J 1), 8.60–8.70 (1H, m), 8.91 (1H, s); m/z (ES$^+$) 330 (M$^+$+H).

EXAMPLE 12

3-[3-(Pyridin-3-yl)phenyl]imidazo[1,2-α]pyridin-7-ylmethanol

3-[3-(Pyridin-3-yl)phenyl]imidazo[1,2-α]pyridine-7-carboxylic acid methyl ester (2.0 g, 6.1 mmol) was suspended in tetrahydrofuran (75 ml) and cooled to 0° C. before adding lithium aluminium hydride (9.1 ml of 1.0M solution in tetrahydrofuran) dropwise over 5 minutes. The mixture was allowed to warm to ambient temperature and stirring continued for 2 h. Sodium sulphate decahydrate (10 g) was then added portionwise and the resulting suspension stirred for a further 1 h. The mixture was diluted with methanol and pre-adsorbed on to silica. Purification by flash column chromatography on silica eluting with dichloromethane/methanol/conc. ammonia (gradient 99:1:0.1 through to 95:5:0.3) gave the title compound (1.25 g, 68%) as a white solid. $^1$H NMR (360 MHz, CDCl$_3$) $\delta_H$ 4.78 (2H, s), 6.87 (1H, dd, J 7 and 1), 7.37–7.43 (1H, m), 7.56–7.75 (6H, m), 7.89–7.95 (1H, m), 8.33 (1H, d, J 7), 8.63 (1H, dd, J 1 and 7), 8.89 (1H, s); m/z (ES$^+$) 302 (M$^+$+H).

EXAMPLE 13

3-[3-(Pyridin-3-yl)phenyl]imidazo[1,2-α]pyridine-7-carboxaldehyde

A suspension of 3-[3-(pyridin-3-yl)phenyl]imidazo[1,2-α]pyridin-7-ylmethanol (67 mg, 0.22 mmol) in 1,2-dichloroethane (5 ml) was treated with manganese(IV) oxide (0.19 g, 2.2 mmol) and the mixture heated at 50° C. for 18 h. The reaction was cooled to ambient temperature, diluted with 1,2-dichloroethane and pre-adsorbed onto silica. Purification by silica gel chromatography eluting with dichloromethane/methanol/conc. ammonia (95:5:0.5) gave the title compound (38 mg, 58%) as a yellow solid. $^1$H NMR (360 MHz, CDCl$_3$) $\delta_H$ 7.36–7.45 (2H, m), 7.60–7.73 (3H, m), 7.76–7.78 (1H, m), 7.90–7.95 (1H, m), 7.97 (1H, s), 8.20 (1H, s), 8.40 (1H, d, J 7), 8.65 (1H, d, J 5), 8.90 (1H, s), 10.00 (1H, s); m/z (ES$^+$) 300 (M$^+$+H).

EXAMPLE 14

3-[3-(Pyridin-3-yl)phenyl]imidazo[1,2-α]pyridine-7-carboxaldehyde oxime

3-[3-(Pyridin-3-yl)phenyl]imidazo[1,2-α]pyridine-7-carboxaldehyde (0.30 g, 1.0 mmol) and hydroxylamine hydrochloride (0.208 g, 3.0 mmol) were suspended in ethanol (15 ml) then heated at 60° C. for 45 min. The mixture was diluted with 50% methanol in dichloromethane (200 ml) and pre-adsorbed onto silica. Purification by flash column chromatography on silica gel eluting with dichloromethane/methanol/conc. ammonia (95:5:0.5) gave the title compound (297 mg, 94%) as a white foam. Further purification of this material by preparative thin-layer chromatography eluting with dichloromethane/methanol/conc. ammonia (95:5:0.5) gave (E)-3-[3-(pyridin-3-yl)phenyl]imidazo[1,2-α]pyridine-7-carboxaldehyde oxime as a white solid followed by (Z)-3-[3-(pyridin-3-yl)phenyl]imidazo[1,2-α]pyridine-7-carboxaldehyde oxime also as a white solid.

(E)-isomer: $^1$H NMR (400 MHz, d$_6$-DMSO) δ$_H$ 7.30 (1H, dd, J 1 and 7), 7.49–7.54 (1H, m), 7.66–7.82 (4H, m), 7.94 (1H, s), 8.00 (1H, s), 8.18–8.23 (1H, m), 8.25 (1H, s, HC=N—OH), 8.59–8.65 (2H, m), 9.01 (1H, d, J 2), 11.52 (1H, s, OH); m/z (ES$^+$) 315 (M$^+$+H). Irradiation of the signal at 11.52 ppm only enhanced the signal at 8.25 ppm.

(Z)-isomer: $^1$H NMR (400 MHz, d$_6$-DMSO) δ$_H$ 7.51–7.61 (3H, m, ArH), 7.68–7.82 (3H, m), 8.01 (2H, s), 8.19–8.24 (1H, m), 8.31 (1H, s, HC=N—OH), 8.60–8.66 (1H, m), 8.69–8.77 (1H, m), 9.02 (1H, s), 11.97 (1H, s, OH); m/z (ES$^+$) 315 (M$^+$+H). Irradiation of the signal at 11.97 ppm enhanced signals within the multiplet at 7.51–7.61 ppm and also the signal at 8.31 ppm.

EXAMPLE 15

3-[3-(Pyridin-3-yl)phenyl]imidazo[1,2-α]pyridine-7-carboxaldehyde O-(2-hydroxyethyl)oxime The title compound was prepared in a similar manner to that described in Example 14 using O-(2-hydroxyethyl) hydroxylamine hydrochloride and 3-[3-(pyridin-3-yl) phenyl]imidazo[1,2-α]pyridine-7-carboxaldehyde to afford a white crystalline solid, essentially as a single geometric isomer, m.p. 149–151° C. $^1$H NMR (400 MHz, CDCl$_3$) δ$_H$ 2.20 (1H, br s), 3.93–3.97 (2H, m), 4.32–4.36 (2H, m), 7.28 (1H, dd, J 2 and 7), 7.37–7.44 (1H, m), 7.58–7.68 (4H, m), 7.75 (1H, s), 7.80 (1H, s), 7.90–7.95 (1H, m), 8.17 (1H, s), 8.31 (1H, d, J 7), 8.63–8.67 (1H, m), 8.90 (1H, s); m/z (ES$^+$) 359 (M$^+$+H).

EXAMPLE 16

3-[3-(Pyridin-3-yl)phenyl]imidazo[1,2-α]pyridine-7-carboxaldehyde O-(2-dimethylaminoethyl)oxime The title compound was prepared in a similar manner to that described in Example 14 using O-(2-dimethylaminoethyl)hydroxylamine hydrochloride and 3-[3-(pyridin-3-yl)phenyl]imidazo[1,2-α]pyridine-7-carboxaldehyde to afford a brown oil, essentially as a single geometric isomer. $^1$H NMR (400 MHz, CDCl$_3$) δ$_H$ 2.97 (6H, s), 3.43–3.47 (2H, m), 4.65–4.69 (2H, m), 7.28–7.33 (2H, m), 7.42–7.47 (1H, m), 7.62–7.82 (4H, m), 7.94–7.98 (1H, m), 8.20 (1H, s), 8.32–8.35 (1H, m), 8.25 (1H, s), 8.61–8.65 (1H, m), 8.90 (1H, s); m/z (ES$^+$) 386 (M$^+$+H).

EXAMPLE 17

1-[3-(3-(Pyridin-3-yl)phenyl)imidazo[1,2-α]pyridin-7-yl]ethanol

3-[3-(Pyridin-3-yl)phenyl]imidazo[1,2-α]pyridine-7-carboxaldehyde (100 mg, 0.33 mmol) in tetrahydrofuran (10 ml) was cooled to −78° C. before adding methylmagnesium bromide (1.3 ml of 0.3M solution in diethyl ether) dropwise over 10 min. Once addition was complete the reaction was allowed to warm to ambient temperature and stirring continued for 16 h. Methanol (1 ml) was added and the mixture partitioned between ethyl acetate and 10% ammonium chloride solution. The organic layer was washed with brine, dried over sodium sulphate and concentrated to give a yellow oil. This oil was purified by preparative thin layer chromatography eluting with dichloromethane/methanol/conc. ammonia (95:5:0.5) to afford the title compound (59 mg, 57%) as a white foam. $^1$H NMR (360 MHz, CDCl$_3$) δ$_H$ 1.55 (3H, d, J 6), 4.97 (1H, q, J 6), 6.91 (1H, dd, J 2 and 7) 7.37–7.43 (1H, m), 7.56–7.67 (4H, m), 7.65–7.74 (2H, m), 7.89–7.94 (1H, m), 8.33 (1H, d, J 7), 8.60–8.65 (1H, m), 8.89 (1H, s); m/z (ES$^+$) 316 (M$^+$+H).

EXAMPLE 18

1-[3-(3-(Pyridin-3-yl)phenyl)imidazo[1,2-α]pyridin-7-yl]ethanone

1-[3-(3-(Pyridin-3-yl)phenyl)imidazo[1,2-α]pyridin-7-yl]ethanol (53 mg, 0.17 mmol) was suspended in 1,2-dichloroethane (2 ml), manganese(IV) oxide (73 mg, 0.84 mmol) added and the mixture heated at 50° C. for 18 h. The mixture was cooled to room temperature, filtered through Celite®, diluted with 1,2-dichloroethane and pre-adsorbed onto silica. Purification by silica gel chromatography eluting with dichloromethane/methanol/conc. ammonia (98:2:0.2) gave the title compound (44 mg, 85%) as a yellow solid. $^1$H NMR (400 MHz, CDCl$_3$) δ$_H$ 2.69 (3H, s), 7.40–7.48 (2H, m), 7.60–7.73 (3H, m), 7.77 (1H, d, J 1), 7.90–7.95 (2H, m), 8.30 (1H, s), 8.38 (1H, dd, J 1 and 7), 8.65–8.67 (1H, m), 8.91 (1H, s); m/z (ES$^+$) 314 (M$^+$+H).

EXAMPLE 19

1-[3-(3-(Pyridin-3-yl)phenyl)imidazo[1,2-α]pyridin-7-yl]ethanone oxime

The title compound was prepared in a similar manner to that described in Example 14 to afford a white crystalline solid, m.p. 227–228° C. $^1$H NMR (400 MHz, CDCl$_3$) δ$_H$ 2.38 (3H, s), 7.21–7.25 (1H, m), 7.40–7.44 (1H, m), 7.61–7.67 (3H, m), 7.78 (1H, s), 7.81 (1H, s), 7.92–7.96 (1H, m), 8.35 (1H, d, J 7), 8.61–8.67 (2H, m), 8.91 (1H, s), 12.23 (1H, br s); m/z (ES+) 329 (M$^+$+H).

EXAMPLE 20

7-Chloro-3-[3-(pyridin-3-yl)phenyl]imidazo[1,2-α] pyridine

A suspension of 2-picolinic acid (123.1 g, 1 mol), thionyl chloride (400 ml) and water (18 ml, 1 mol) were heated at reflux for 96 h. The mixture was cooled, evaporated to dryness and azeotroped with toluene (2×500 ml). The residue was dissolved in toluene (1 l) and cooled to 5° C. before dropwise addition of methanol (44 g, 1.3 mol) over 30 min, which gave a white precipitate. The solid was filtered, washed with toluene (3×100 ml) and dried at 40° C. under vacuum to give 4-chloropyridine-2-carboxylic acid methyl ester as its hydrochloride salt (160 g, 77%) as a pale yellow solid. $^1$H NMR (400 MHz, d$_6$-DMSO) δ$_H$ 7.84 (1H, dd, J 2 and 5), 8.12 (1H, d, J 2), 8.71 (1H, d, J 5).

A solution of 4-chloropyridine-2-carboxylic acid methyl ester hydrochloride (30.0 g, 0.144 mol) in methanol (150 ml) was treated with hydrazine hydrate (63 ml) added portionwise over 20 min and the resulting suspension was stirred at room temperature for 2 h. The hydrazide was isolated by filtration to give a white powder. This product was dissolved in 1M hydrochloric acid (135 ml) and cooled to 0° C. before a solution of sodium nitrite (11.2 g, 0.162 mol) in water (50 ml) was added dropwise at such a rate to keep the internal temperature below 5° C. (ca. 45 min). Once addition was complete the resulting precipitate was stirred for 15 min then the acyl azide was collected by filtration. The moist solid was then added portionwise to a hot (80° C.) solution of 50% glacial acetic acid in water (250 ml) and stirring continued for 1 h. The mixture was cooled, made basic with conc. ammonia and extracted into ethyl acetate (2×300 ml). The combined organic layers were washed with brine, dried over sodium sulphate and evaporated to give 4-chloropyridin-2-ylamine (8.2 g, 44%) as a white crystalline solid. $^1$H NMR (400 MHz, CDCl$_3$) δ$_H$ 4.55 (2H, br s), 6.50 (1H, s), 6.65 (1H, dd, J 2 and 5), 7.96 (1H, d, J 5).

A stirred suspension of 4-chloropyridin-2-ylamine (6.20 g, 48.2 mmol), chloroacetaldehyde (11.4 g of a 50 wt % solution in water, 73 mmol) and sodium hydrogencarbonate (8.09 g, 96.4 mmol) in ethanol (70 ml) was heated under reflux for 6 h. The solvent was evaporated and the residue partitioned between ethyl acetate and water. The organic layer was washed with brine, dried over sodium sulphate and concentrated in vacuo to give an orange oil. This oil was purified by silica gel chromatography eluting with 50% ethyl acetate in isohexane to afford 7-chloroimidazo[1,2-α]pyridine (5.60 g, 75%) as a white crystalline solid. $^1$H NMR (400 MHz, CDCl$_3$) $\delta_H$ 6.78 (1H, d, J 7), 7.56 (1H, s), 7.63 (2H, s), 8.05 (1H, d, J 7).

7-Chloroimidazo[1,2-α]pyridine (3.0 g, 19.7 mmol) and sodium acetate (1.94 g, 23.6 mmol) were dissolved in a saturated solution of potassium bromide in methanol (25 ml) and cooled to 0° C. before adding bromine (3.3 g, 20.7 mmol) dropwise over 5 min. The mixture was allowed to stir for 15 min before pouring onto saturated sodium hydrogencarbonate solution (200 ml). The resulting solid was collected by filtration and dried under high vacuum to give 3-bromo-7-chloroimidazo[1,2-α]pyridine (3.64 g, 80%) as a white solid. $^1$H NMR (360 MHz, CDCl$_3$) $\delta_H$ 6.92 (1H, dd, J 2 and 7), 7.61 (1H, s), 7.63 (1H, d, J 2), 8.05 (1H, d, J 7).

The title compound was prepared in a similar manner to that described in Example 11 from 3-bromo-7-chloroimidazo[1,2-α]pyridine and 3-[3-(tri-n-butylstannanyl)phenyl]pyridine. Oxalate salt, white crystalline solid, m.p. 178–180° C. (EtOH). $^1$H NMR (360 MHz, d$_6$-DMSO) $\delta_H$ 7.05 (1H, dd, J 7 and 2), 7.50–7.56 (1H, m), 7.67–7.89 (4H, m), 7.96 (1H, s), 8.01 (1H, s), 8.21 (1H, d, J 7), 8.61 (1H, d, J 4), 8.70 (1H, d, J 7), 9.02 (1H, d, J 2); m/z (ES$^+$) 306 (M$^+$+H).

EXAMPLE 21

7-(Furan-3-yl)-3-[3-(pyridin-3-yl)phenyl]imidazo[1,2-α]pyridine

7-Chloro-3-[3-(pyridin-3-yl)phenyl]imidazo[1,2-α]pyridine (0.27 g, 0.88 mmol), 3-furanboronic acid (0.15 g, 1.33 mmol and caesium carbonate (0.58 g, 1.77 mmol) were suspended in 1,4-dioxane (5 ml) under an atmosphere of nitrogen. Tris(dibenzylideneacetone)dipalladium(0) (12 mg, 0.015 mmol) and tri-tert-butylphosphine (6.5 mg, 0.032 mmol) were then added and the mixture heated at 90° C. for 24 h. The mixture was cooled and partitioned between dichloromethane and water. The organic layer was washed with brine, dried over sodium sulphate and concentrated in vacuo to give a brown oil. Purification by flash column chromatography eluting with dichloromethane/methanol/conc. ammonia (98:2:0.2) gave the title compound (110 mg, 37%) as a pale yellow crystalline solid, m.p. 158–160° C. $^1$H NMR (360 MHz, CDCl$_3$) $\delta_H$ 6.79 (1H, s), 6.96–7.02 (1H, m), 7.39–7.43 (1H, m), 7.52–7.56 (1H, m), 7.59–7.69 (2H, m), 7.75–7.91 (8H, m), 8.32–8.37 (1H, m), 8.63–8.68 (1H, m), 8.92 (1H, s); m/z (ES$^+$) 338 (M$^+$+H).

EXAMPLE 22

7-Methoxy-3-[3-(pyridin-3-yl)phenyl]imidazo[1,2-α]pyridine

4-Chloropyridine-2-carboxylic acid methyl ester hydrochloride (25 g, 0.12 mol) was dissolved in methanol (200 ml) and heated at reflux for 66 h. The solvent was evaporated and the residue partitioned between dichloromethane and saturated sodium hydrogencarbonate solution. The organic layer was washed with brine, dried over sodium sulphate and concentrated to give 4-methoxypyridine-2-carboxylic acid methyl ester (17.6 g, 88%) as a yellow crystalline solid. $^1$H NMR (360 MHz, CDCl$_3$) $\delta_H$ 3.91 (3H, s), 4.02 (3H, s), 6.98 (1H, dd, J 3 and 6), 7.67 (1H, d, J 3), 8.54 (1H, d, J 6).

4-Methoxypyridine-2-carboxylic acid methyl ester (17.6 g, 0.105 mol) was dissolved in methanol (100 ml) and cooled to 0° C. before adding hydrazine hydrate (21 ml) dropwise over 10 min. The mixture was then refrigerated at 4° C. for 16 h. The resulting solid was filtered, washed with cold methanol and dried to afford 4-methoxypyridine-2-carboxylic acid hydrazide (14.3 g, 81%) as a white powder. $^1$H NMR (360 MHz, CDCl$_3$) $\delta_H$ 3.89 (3H, s), 4.55 (2H, br s), 7.12 (1H, dd, J 3 and 6), 7.50 (1H, d, J 3), 8.42 (1H, d, J 6), 9.79 (1H, br s).

To a cooled (0° C.) suspension of 4-methoxypyridine-2-carboxylic acid hydrazide (10.0 g, 59.9 mmol) and trifluoroacetic acid (6.83 g, 59.9 mmol) in tetrahydrofuran (120 ml) was added tert-butylnitrite (18.52 g, 179.6 mmol) at such a rate to keep the internal temperature below 5° C. (ca. 45 min). Once addition was complete the mixture was allowed to stir at 0° C. for 30 min and then the solvent was removed in vacuo. Toluene (100 ml) was added and the mixture heated under reflux for 1 h before adding tert-butanol (15 ml, 155.7 mmol). After heating at reflux for a further 10 h the reaction was cooled and the solvent evaporated in vacuo. The residue was suspended in toluene (100 ml), trifluoroacetic acid (5 ml) was added and the mixture heated at reflux for 5 h. The solvent was removed on a rotary evaporator and the residue purified by flash column chromatography on silica eluting with dichloromethane/methanol/conc. ammonia (97:3:0.3) to furnish 4-methoxypyridin-2-ylamine (4.50 g, 61%) as a pale brown solid. $^1$H NMR (400 MHz, CDCl$_3$) $\delta_H$ 3.90 (3H, s), 6.12 (1H, s), 6.32 (1H, d, J 7), 7.52 (1H, d, J 7), 7.75 (1H, br s).

A stirred suspension of 4-methoxypyridin-2-ylamine (4.50 g, 36.3 mmol), chloroacetaldehyde (8.54 g of a 50 wt % solution in water, 54.4 mmol) and sodium hydrogencarbonate (6.09 g, 72.6 mmol) in ethanol (70 ml) was heated under reflux for 4 h. The solvent was evaporated and the residue partitioned between ethyl acetate and water. The organic layer was washed with brine, dried and evaporated to give an orange oil. Purification by silica gel chromatography eluting with 2% methanol in dichloromethane gave 7-methoxyimidazo[1,2-α]pyridine (2.40 g, 45%) as a brown oil. $^1$H NMR (400 MHz, CDCl$_3$) $\delta_H$ 3.85 (3H, s), 6.50 (1H, d, J 7), 6.88 (1H, s), 7.41 (1H, s), 7.48 (1H, s), 7.92 (1H, d, J 7).

7-Methoxyimidazo[1,2-α]pyridine (1.0 g, 6.8 mmol) and sodium acetate (0.67 g, 8.1 mmol) were dissolved in a saturated solution of potassium bromide in methanol (5 ml) and cooled to 0° C. before adding bromine (1.13 g, 7.1 mmol) dropwise over 5 min. The mixture was allowed to stir for 15 min before pouring onto saturated sodium hydrogencarbonate solution (50 ml). The resulting yellow solid was collected by filtration and dried. This solid was purified by flash column chromatography on silica eluting with 50% ethyl acetate in isohexane to afford 3-bromo-7-methoxyimidazo[1,2-α]pyridine (0.4 g, 26%) as a white solid. $^1$H NMR (360 MHz, CDCl$_3$) $\delta_H$ 3.87 (3H, s), 6.64 (1H, dd, J 2 and 7), 6.88 (1H, d, J 2), 7.45 (1H, s), 7.92 (1H, d, J 7).

The title compound was prepared in a similar manner to that described in Example 11 from 3-bromo-7-methoxyimidazo[1,2-α]pyridine and 3-[3-(tri-n-butylstannanyl)phenyl]pyridine to furnish a white crystalline solid, m.p. 153–154° C. ¹H NMR (360 MHz, CDCl₃) $\delta_H$ 3.89 (3H, s), 6.57 (1H, dd, J 2 and 8), 6.94 (1H, d, J 2), 7.37–7.43 (1H, m), 7.55–763 (4H, m), 7.72 (1H, s), 7.89–7.94 (1H, m), 8.19 (1H, d, J 7), 8.62–8.65 (1H, m), 8.90 (1H, s); m/z (ES⁺) 302 (M⁺+H).

EXAMPLE 23

3'-(7-Methylimidazo[1,2-α]pyridin-3-yl)biphenyl-2-carbonitrile

Prepared by a method analogous to that described in Example 1. ¹H NMR (360 MHz, CDCl₃) $\delta_H$ 2.42 (3H, s), 6.73 (1H, dd, J 7 and 1.5), 7.43–7.82 (10H, m), 8.46 (1H, d, J 7); m/z (ES⁺) 310 (M⁺+H).

EXAMPLE 24

3-[3-(7-Methylimidazo[1,2-α]pyridin-3-yl)phenyl]thiophene-2-carboxamide

Prepared by a method analogous to that described in Example 1. M.p. 203–205° C. ¹H NMR (360 MHz, d₆-DMSO) $\delta_H$ 2.39 (3H, s), 6.85 (1H, dd, J 7 and 1.5), 7.31 (1H, d, J 5), 7.44–7.62 (6H, m), 7.70–7.73 (3H, m), 8.57 (1H, d, J 7); m/z (ES⁺) 334 (M⁺+H).

EXAMPLE 25

3-[3-(2-Cyanothien-3-yl)phenyl]imidazo[1,2-α]pyridine-7-carboxylic acid methyl ester A mixture of 3-bromothiophene-2-carbonitrile (5.64 g, 30 mmol), 3-hydroxyphenylboronic acid (6.21 g, 45 mmol) and tetrakis(triphenylphosphine)palladium(0) (1.04 g, 0.9 mmol) in 1,2-dimethoxyethane (75 ml) and 2M aqueous sodium carbonate (25 ml) was heated at 80° C. for 20 h. After cooling to ambient temperature the reaction was made acidic (pH 6) with 1N hydrochloric acid and then partitioned between ethyl acetate (250 ml) and water (200 ml). The organics were washed with brine, dried over anhydrous sodium sulfate, filtered and pre-adsorbed onto silica. Purification by flash chromatography eluting with isohexane on a gradient of ethyl acetate (10–30%) gave recovered 3-bromothiophene-2-carbonitrile (2.4 g) followed by 3-(3-hydroxyphenyl)thiophene-2-carbonitrile as a pale yellow oil that solidified on standing (3.0 g, 50%). ¹H NMR (360 MHz, d₆-DMSO) $\delta_H$ 5.55 (1H, br), 6.90–6.93 (1H, m), 7.19–7.37 (4H, m), 7.60 (1H, d, J 5).

To a cooled (0° C.) suspension of 3-(3-hydroxyphenyl)thiophene-2-carbonitrile (0.63 g, 3.11 mmol) in dry dichloromethane (10 ml) was added dry pyridine (0.5 ml, 6.22 mmol) and the mixture stirred for 15 min. Trifluoromethanesulfonic anhydride (0.78 ml, 4.66 mmol) was added slowly and the reaction mixture stirred for 1 h then allowed to warm to ambient temperature for a further hour before pouring into water (40 ml) and dichloromethane (40 ml). The organic phase was separated, washed with brine (40 ml), dried over anhydrous magnesium sulfate and evaporated onto silica. The residue was purified by flash column chromatography on silica eluting with isohexane on a gradient of ethyl acetate from 10% to 30% to give trifluoromethanesulfonic acid 3-(2-cyanothien-3-yl)phenyl ester as a colourless oil (0.69 g, 66%). ¹H NMR (360 MHz, CDCl₃) $\delta_H$ 7.29 (1H, dd, J 5 and 1), 7.36 (1H, dd, J 8 and 2), 7.56–7.62 (2H, m), 7.67 (1H, d, J 5), 7.76 (1H, dd, J 8 and 1).

Bis(pinacolato)diboron (0.67 g, 2.66 mmol), potassium acetate (0.52 g, 5.31 mmol) and trifluoromethanesulfonic acid 3-(2-cyanothien-3-yl)phenyl ester (0.59 g, 1.77 mmol) were combined and purged with nitrogen. Anhydrous 1,4-dioxane (10 ml) and dichloro[1,1'-bis(diphenylphosphino)ferrocene]palladium(II) (43 mg, 0.05 mmol) were added and the mixture heated at 80° C. for 18 h. The cooled reaction was partitioned between ethyl acetate (150 ml) and water (100 ml). The organic layer was washed with brine, dried over anhydrous sodium sulfate and evaporated to dryness to give 3-[3-(4,4,5,5-tetramethyl[1,3,2]dioxaborolan-2-yl)phenyl]thiophene-2-carbonitrile as a black oil (0.55 g, 100%). This oil was dissolved in sufficient N,N-dimethylacetamide to give a 0.5M stock solution.

3-Bromoimidazo[1,2-α]pyridine-7-carboxylic acid methyl ester (0.63 g, 2.47 mmol) and 3-[3-(4,4,5,5-tetramethyl-[1,3,2]dioxaborolan-2-yl)phenyl]thiophene-2-carbonitrile (0.55 g, 1.76 mmol) were suspended in 1,2-dimethoxyethane (10 ml) and 2N sodium carbonate solution (5 ml) and degassed with nitrogen for 30 min before addition of tetrakis(triphenylphosphine)palladium(0) (0.14 g, 0.12 mmol). The mixture was heated at 80° C. for 18 h then cooled to room temperature. The mixture was partitioned between ethyl acetate (100 ml) and water (50 ml). The organic layer was washed with brine, dried over sodium sulfate and pre-adsorbed onto silica gel. Purification by silica gel chromatography eluting with dichloromethane/methanol/conc. ammonia (gradient 99:1:0.1 through to 97:2:0.2) gave the title compound (0.59 g, 94%) as pale brown needles. ¹H NMR (400 MHz, CDCl₃) $\delta_H$ 3.98 (3H, s), 7.35 (1H, d, J 5), 7.48 (1H, dd, J 7 and 2), 7.65–7.75 (3H, m), 7.93 (2H, m), 8.43 (1H, s), 8.54 (1H, dd, J 7 and 1); m/z (ES⁺) 360 (M⁺+H).

EXAMPLE 26

3-[3-(7-Formylimidazo[1,2-α]pyridin-3-yl)phenyl]thiophene-2-carbonitrile

To a cooled (0° C.) solution of imidazo[1,2-α]pyridine-7-carboxylic acid methyl ester (2.15 g, 12.2 mmol) in methanol (50 ml) was added sodium borohydride (4.64 g, 12.2 mmol) in portions over 15 min. The mixture was heated under reflux for 3 h, cooled to ambient temperature and evaporated to dryness. The residue was dissolved in dichloromethane:methanol (300 ml of a 1:1 mixture) and pre-adsorbed onto silica. Purification by silica gel chromatography eluting with dichloromethane/methanol/conc. ammonia (95:5:0.5) gave imidazo[1,2-α]pyridin-7-ylmethanol (1.75 g, 77%) as a colourless oil. ¹H NMR (400 MHz, CDCl₃) $\delta_H$ 4.71 (2H, s), 6.79 (1H, dd, J 7 and 1), 7.37 (1H, s), 7.52 (1H, s), 7.56 (1H, d, J 1), 8.05 (1H, d, J 7).

Imidazo[1,2-α]pyridin-7-ylmethanol (1.35 g, 9.38 mmol) was suspended in 1,2-dichloroethane (40 ml), manganese (IV) oxide (4.07 g, 46.9 mmol) added and the mixture heated at 50° C. for 16 h. The mixture was cooled to ambient temperature, filtered through Celite® and evaporated to dryness to give imidazo[1,2-α]pyridine-7-carboxaldehyde (0.92 g, 69%) as a yellow solid. ¹H NMR (400 MHz, CDCl₃) $\delta_H$ 7.34 (1H, dd, J 7 and 1), 7.75 (1H, s), 7.87 (1H, s), 8.13 (1H, s), 8.21 (1H, d, J 7), 10.00 (1H, s).

Imidazo[1,2-α]pyridine-7-carboxaldehyde (0.92 g, 9.38 mmol) and sodium acetate (0.62 g, 7.52 mmol) were dissolved in a saturated solution of potassium bromide in methanol (20 ml) and cooled to 0° C. before dropwise addition of bromine (1.05 g, 6.58 mmol) over 5 min. The mixture was allowed to stir for 15 minutes before adding saturated sodium sulphite solution (1 ml). The reaction was evaporated to dryness and the residue partitioned between ethyl acetate and 10% sodium sulfate solution. The organics were washed with water, brine, dried over sodium sulfate and concentrated to give a yellow oil. This oil was purified by flash column chromatography on silica eluting with dichloromethane/methanol/conc. ammonia (gradient 99:1:0.1 through to 97:3:0.3) to give 3-bromo-imidazo[1,2-α]pyridine-7-carboxaldehyde (1.20 g, 85%) as a yellow solid. $^1$H NMR (360 MHz, CDCl$_3$) $\delta_H$ 7.47 (1H, dd, J 7 and 1), 7.84 (1H, s), 8.12 (1H, d, J 2), 8.36 (1H, d, J 7 and 1), 10.03 (1H, s).

3-Bromoimidazo[1,2-α]pyridine-7-carboxaldehyde (1.15 g, 5.16 mmol), potassium phosphate (2.19 g, 10.31 mmol) and 3-[3-(4,4,5,5-tetramethyl-[1,3,2]dioxaborolan-2-yl)phenyl]thiophene-2-carbonitrile (2.58 g, 8.26 mmol) were dissolved in N,N-dimethylacetamide (15 ml) and the mixture degassed with N$_2$ for 15 min. Tetrakis(triphenylphosphine)pallidum(0) (0.30 g, 0.26 mmol) was added and the mixture heated at 80° C. for 18 h. The mixture was allowed to cool to room temperature, diluted with water (20 ml) and saturated sodium hydrogencarbonate solution (20 ml), then extracted with ethyl acetate (2×75 ml). The combined organic fractions were washed with brine (40 ml), dried over anhydrous sodium sulfate and evaporated to give a black oil. The oil was purified by silica gel chromatography eluting with dichloromethane and 1% conc. ammonia on a gradient of methanol (1–2%). The solid obtained was triturated with diethyl ether which gave the title compound (1.15 g, 68%) as a white powder. Oxalate salt, white powder. 1H NMR (360 MHz, d$_6$-DMSO) $\delta_H$ 7.30 (1H, dd, J 7 and 1), 7.70–7.88 (4H, m), 8.08 (1H, s), 8.16–8.22 (2H, m), 8.44 (1H, s), 8.78 (1H, d, J 7), 10.05 (1H, s); m/z (ES$^+$) 330 (M$^+$+H).

EXAMPLE 27

3-[3-(7-Hydroxyiminomethylimidazo[1,2-α]pyridin-3-yl)phenyl]thiophene-2-carbonitrile The title compound was prepared in a similar manner to that described in Example 14 using hydroxylamine hydrochloride (57 mg, 0.82 mmol) and 3-[3-(7-formylimidazo[1,2-α]pyridin-3-yl)phenyl]thiophene-2-carbonitrile (90 mg, 0.27 mmol) to afford a white crystalline solid (77 mg, 82%), essentially as a single geometric isomer, m.p. >230° C. $^1$H NMR (360 MHz, d$_6$-DMSO) $\delta_H$ 7.27 (1H, dd, J 1 and 7), 7.70–7.82 (3H, m), 7.91 (1H, s), 8.03 (1H, s), 8.17 (1H, d, J 1), 7.90–7.95 (1H, m), 8.17 (1H, d, J 5), 8.31 (1H, s), 8.65 (1H, d, J 7), 11.53 (1H, s); m/z (ES$^+$) 345 (M$^+$+H).

EXAMPLE 28

3-[3-(7-(2-Hydroxyethoxy)iminomethylimidazo[1,2-α]pyridin-3-yl)phenyl]thiophene-2-carbonitrile The title compound was prepared in a similar manner to that described in Example 14 using O-(2-hydroxyethyl)hydroxylamine hydrochloride (93 mg, 0.82 mmol) and 3-[3-(7-formylimidazo[1,2-α]pyridin -3-yl)phenyl]thiophene-2-carbonitrile (67 mg, 0.20 mmol) to afford a white crystalline solid (43 mg, 55%), essentially as a single geometric isomer, m.p. 224–225° C. $^1$H NMR (360 MHz, CDCl$_3$) $\delta_H$ 3.94–3.97 (2H, m), 4.32–4.36 (2H, m), 7.31–7.38 (2H, m), 7.64–7.72 (5H, m), 7.80 (1H, s), 7.88 (1H, s), 8.17 (1H, s), 8.47 (1H, d, J 7); m/z (ES$^+$) 389 (M$^+$+H).

EXAMPLE 29

3-[3-(7-(2-Dimethylaminoethoxy)iminomethylimidazo[1,2-α]pyridin-3-yl)phenyl]thiophene-2-carbonitrile The title compound was prepared in a similar manner to that described in Example 14 using O-(2-dimethylaminoethyl)hydroxylamine hydrochloride (144 mg, 0.82 mmol) and 3-[3-(7-formylimidazo[1,2-α]pyridin-3-yl)phenyl]thiophene-2-carbonitrile (90 mg, 0.27 mmol) to afford a yellow solid (42 mg, 38%), essentially as a single geometric isomer, m.p. 74–75° C. $^1$H NMR (360 MHz, CDCl$_3$) $\delta_H$ 2.33 (6H, s), 2.67–2.71 (2H, m), 4.30–4.34 (2H, m), 7.33–7.37 (2H, m), 7.63–7.70 (4H, m), 7.79 (1H, s), 7.91 (1H, s), 8.15 (1H, s), 8.45 (1H, d, J 7); m/z (ES$^+$) 416 (M$^+$+H).

EXAMPLE 30

3'-(7-Formylimidazo[1,2-α]pyridin-3-yl)biphenyl-2-carbonitrile

A mixture of 2-bromobenzonitrile (9.1 g, 50 mmol), 3-aminobenzeneboronic acid monohydrate (11.6 g, 75 mmol) and tetrakis(triphenylphosphine)palladium(0) (1.73 g, 1.5 mmol) in 1,2-dimethoxyethane (50 ml) and 2M sodium carbonate solution (25 ml) was heated at 80° C. for 20h. After cooling to ambient temperature the reaction was partitioned between ethyl acetate (400 ml) and water (400 ml). The organics were washed with brine (400 ml), dried over anhydrous sodium sulfate, filtered and concentrated in vacuo. Purification of the residue by flash chromatography on silica gel, eluting with isohexane on a gradient of ethyl acetate (0–25%) gave 3'-aminobiphenyl-2-carbonitrile as a colourless oil that solidified on standing to afford a white solid (9.5 g, 98%). $^1$H NMR (360 MHz, CDCl$_3$) $\delta_H$ 3.79 (2H, br), 6.75 (1H, ddd, J 8, 3 and 1), 6.84 (1H, dd, J 3 and 3), 6.92 (1H, dd, J 8 and 3), 7.25 (1H, dd, J 8 and 8), 7.40 (1H, ddd, J 8, 8 and 1), 7.50 (1H, dd, J 8 and 1), 7.62 (1H, ddd, J 8, 8 and 1), 7.73 (1H, dd, J8 and 1).

A solution of 3'-aminobiphenyl-2-carbonitrile (10.9 g, 56 mmol) in 1,4-dioxane (30 ml) was treated with a solution of 25% aqueous sulphuric acid (150 ml). The resulting suspension was cooled to 0° C. before being treated dropwise over 10 minutes with a solution of sodium nitrite (4.6 g, 67 mmol) in water (10 ml). After stirring at 0° C. for 30 minutes the reaction was poured into hot (70° C.) water (500 ml). On cooling to ambient temperature the product was extracted into ethyl acetate (500 ml), the organics were washed with water (300 ml), brine (300 ml) and dried over anhydrous sodium sulfate. Filtration and concentration in vacuo afforded 3'-hydroxybiphenyl-2-carbonitrile as a dark oil (7.1 g, 65%). $^1$H NMR (400 MHz, CDCl$_3$) $\delta_H$ 5.40 (1H, br), 6.92 (1H, ddd, J 8, 3 and 1), 7.04 (1H, dd, J 3 and 3), 7.11 (1H, ddd, J 8, 3 and 1), 7.35 (1H, dd, J 8 and 8), 7.44 (1H, ddd, J 8, 8 and 1), 7.51 (1H, dd, J 8 and 1), 7.64 (1H, ddd, J 8, 8 and 1), 7.75 (1H, dd, J 8 and 1).

3'-Hydroxybiphenyl-2-carbonitrile (0.48 g, 2.47 mmol) and dry pyridine (0.98 g, 12.35 mmol) were dissolved in dichloromethane (7 ml) and cooled to 0° C. before dropwise addition of trifluoromethanesulfonic anhydride (1.04 g, 3.70 mmol) over 5 min. The mixture was stirred at 0° C. for 10 min and then at 25° C. for 1 h. The solvent was evaporated in vacuo and the residue partitioned between ethyl acetate (200 ml) and water (150 ml). The organic layer was washed with brine (150 ml), dried over anhydrous sodium sulfate and evaporated to give a brown oil. Purification by silica gel chromatography eluting with isohexane on a gradient of ethyl acetate (0–30%) gave trifluoromethanesulfonic acid 2'-cyanobiphenyl-3-yl ester as a yellow oil (544 mg, 67%). $^1$H NMR (400 MHz, CDCl$_3$) $\delta_H$ 7.37 (1H, ddd, J 8, 3 and 1), 7.39 (1H, dd, J 3 and 3), 7.50–7.60 (2H, m), 7.61–7.65 (2H, m), 7.64 (1H, td, J 8 and 1), 7.80 (1H, dd, J 8 and 1).

Trifluoromethanesulfonic acid 2'-cyanobiphenyl-3-yl ester (0.55 g, 1.66 mmol), potassium acetate (0.49 g, 4.98 mmol) and bis(pinacolato)diboron (0.55 g, 2.16 mmol) were dissolved in 1,4-dioxane (10 ml) and the mixture degassed with N2 for 15 min. Dichloro[1,1'-bis(diphenylphosphino)ferrocene]palladium(II) dichloromethane adduct (41 mg, 0.05 mmol) and 1,1'-bis(diphenylphosphino)ferrocene (28 mg, 0.05 mmol) were then added and the mixture heated at 85° C. for 18 h. The mixture was cooled to ambient temperature and partitioned between ethyl acetate (150 ml) and water (50 ml). The organic layer was washed with brine (50 ml), dried over anhydrous sodium sulfate and evaporated in vacuo to give 3'-(4,4,5,5-tetramethyl-[1,3,2]dioxaborolan-2-yl)biphenyl-2-carbonitrile as a black oil (0.51 g, 100%). This oil was dissolved in sufficient N,N-dimethylacetamide to give a 0.5 M stock solution. 3-Bromoimidazo[1,2-α]pyridine-7-carboxaldehyde (0.70 g, 3.11 mmol), potassium phosphate (0.99 g, 4.67 mmol) and 3'-(4,4,5,5-tetramethyl-[1,3,2]dioxaborolan-2-yl)biphenyl-2-carbonitrile (1.80 g, 5.90 mmol) were dissolved in N,N-dimethylacetamide (6 ml) and the mixture degassed with $N_2$ for 15 min. Tetrakis(triphenylphosphine)palladium(0) (0.14 g, 0.12 mmol) was added and the mixture heated at 80° C. for 18 h. The mixture was allowed to cool to room temperature, diluted with water (20 ml) and saturated sodium hydrogencarbonate solution (20 ml), then extracted with ethyl acetate (3×75 ml). The combined organic fractions were washed with brine (40 ml), dried over anhydrous sodium sulfate and evaporated to give a black oil. The oil was purified by silica gel chromatography eluting with dichloromethane and 1% conc. ammonia on a gradient of methanol (1–3%). The solid obtained was triturated with diethyl ether which gave the title compound (0.33 g, 29%) as a yellow powder. $^1$H NMR (400 MHz, CDCl$_3$) $\delta_H$ 7.41 (1H, dd, J 7 and 1), 7.52 (1H, dt, J 8 and 1), 7.58 (1H, d, J 7), 7.62–7.73 (4H, m), 8.81–8.44 (2H, m), 7.98 (1H, s), 8.18 (1H, d, J 1), 8.63 (1H, d, J 7), 10.03 (1H, s); m/z (ES$^+$) 324 (M$^+$+H).

EXAMPLE 31

3'-(7-Hydroxyiminomethylimidazo [1,2-α]pyridin-3-yl)biphenyl-2-carbonitrile

The title compound was prepared in a similar manner to that described in Example 14 using hydroxylamine hydrochloride (77 mg, 1.11 mmol) and 3'-(7-formylimidazo[1,2-α]pyridin-3-yl)biphenyl-2-carbonitrile (120 mg, 0.37 mmol) to afford a white crystalline solid (105 mg, 83%), essentially as a single geometric isomer. $^1$H NMR (400 MHz, d$_6$-DMSO) $\delta_H$ 7.27 (1H, dd, J 1 and 7), 7.61–7.90 (8H, m), 7.90 (2H, s), 8.00 (1H, dd, J 8 and 1), 8.25 (1H, s), 8.68 (1H, d, J 7), 11.53 (1H, s); m/z (ES$^+$) 339 (M$^+$+H).

EXAMPLE 32

3-(2'-Cyanobiphenyl-3-yl)imidazo[1,2-α]pyridine-7-carbonitrile

3'-(7-Hydroxyiminomethylimidazo[1,2-α]pyridin-3-yl)biphenyl-2-carbonitrile (105 mg, 0.31 mmol), triethylamine (157 mg, 1.55 mmol) and 1,1'-carbonyldiimidazole (252 mg, 1.55 mmol) were dissolved in dichloromethane (5 ml) and stirred at room temperature for 15 min then heated under reflux for 2.5 h. The mixture was cooled to ambient temperature, diluted with dichloromethane (40 ml) and washed with water (40 ml) and brine (40 ml). The organics were dried over anhydrous sodium sulfate and evaporated to dryness. Purification of this material by preparative thin-layer chromatography eluting with dichloromethane/methanol/conc. ammonia (98:2:0.2) gave the title compound (85 mg, 86%) as a white solid. $^1$H NMR (400 MHz, CDCl$_3$) $\delta_H$ 7.03 (1H, dd, J 1 and 7), 7.52 (1H, dt, J 8 and 1), 7.58 (1H, d, J 7), 7.62–7.66 (2H, m), 7.69–7.74 (2H, m), 7.79–7.84 (2H, m), 7.97 (1H, s), 8.12 (1H, s), 8.69 (1H, d, J 7); m/z (ES$^+$) 321 (M$^+$+H).

EXAMPLE 33

3'-(7-Difluoromethylimidazo[1,2-α]pyridin-3-yl)biphenyl-2-carbonitrile

To a cooled (0° C.) solution of 3'-(7-formylimidazo[1,2-α]pyridin-3-yl)biphenyl-2-carbonitrile (100 mg, 0.31 mmol) and ethanol (1.4 mg, 0.031 mmol) in dichloromethane (5 ml) was added (diethylamino)sulfur trifluoride (0.125 mg, 0.77 mmol) dropwise over 5 min. The mixture was allowed to warm to room temperature then heated under reflux for 24 h. The mixture was cooled to ambient temperature, quenched by the addition of saturated sodium hydrogencarbonate solution (5 ml), diluted with water (40 ml) and extracted with dichloromethane (70 ml). The organics were washed with brine (40 ml), dried over anhydrous sodium sulfate and evaporated to dryness. The oil was purified by silica gel chromatography eluting with dichloromethane and 1% conc. ammonia on a gradient of methanol (1–2%). The solid obtained was triturated with diethyl ether which gave the title compound (52 mg, 49%) as a white powder. $^1$H NMR (400 MHz, CDCl$_3$) $\delta_H$ 6.70 (1H, t, J 56), 7.02 (1H, dd, J 7 and 2), 7.50 (1H, dt, J 8 and 1), 7.58 (1H, dt, J 7 and 2), 7.63–7.72 (4H, m), 7.79–7.84 (3H, m), 7.85 (1H, s), 8.67 (1H, d, J 7); m/z (ES$^+$) 346 (M$^+$+H).

EXAMPLE 34

3'-(7-Hydroxymethylimidazo[1,2-α]-pyridin3-yl)biphenyl-2-carbonitrile

3'-(7-Formylimidazo[1,2-α]pyridin-3-yl)biphenyl-2-carbonitrile (140 mg, 0.43 mmol) was suspended in chloroform (4 ml) and methanol (7 ml), sodium borohydride (82 mg, 2.17 mmol) added portionwise over 5 min then the reaction was heated under reflux for 1.5 h. The mixture was evaporated to dryness, the residue diluted with water (40 ml) and extracted with chloroform (2×50 ml). The combined organics were washed with brine (40 ml), dried over anhydrous sodium sulfate and evaporated to dryness. Purification was effected by silica gel chromatography eluting with dichloromethane and 1% conc. ammonia on a gradient of methanol (1–5%). The solid obtained was triturated with diethyl ether which gave the title compound (106 mg, 75%) as a white powder. $^1$H NMR (400 MHz, MeOD) $\delta_H$ 4.70 (2H, d, J 1), 6.97 (1H, dd, J 7 and 2), 7.55–7.60 (2H, m), 7.61–7.65 (1H, m), 7.67–7.80 (5H, m), 7.84–7.88 (2H, m), 8.65 (1H, dd, J 7 and 1); m/z (ES$^+$) 326 (M$^+$+H).

EXAMPLE 35

3'-(7-Fluoromethylimidazo[1,2-α]pyridin-3-yl)biphenyl-2-carbonitrile

To a cooled (−78° C.) suspension of 3'-(7-hydroxymethylimidazo[1,2-α]pyridin-3-yl)biphenyl-2-carbonitrile (96 mg, 0.30 mmol) in dichloromethane (20 ml) was added (diethylamino)sulfur trifluoride (50 mg, 0.31 mmol) dropwise over 5 min. The mixture was stirred at −78° C. for 20 min then allowed to warm to −40° C. for 5 min before quenching the reaction with a pre-cooled −40° C. solution of acetic acid (0.5 ml) in dichloromethane (5 ml). The mixture was warmed to ambient temperature, made basic with saturated sodium hydrogencarbonate solution (30 ml) and extracted with dichloromethane (2×75 ml). The combined organics were washed with brine (30 ml), dried over anhydrous sodium sulfate and evaporated to dryness. Purification by silica gel chromatography eluting with dichloromethane and 1% conc. ammonia on a gradient of methanol (1–2%) gave a solid which was triturated with diethyl ether to give the title compound (84 mg, 87%) as a white powder. $^1$H NMR (400 MHz, CDCl$_3$) $\delta_H$ 5.45 (2H, d, J 47), 6.90 (1H, dd, J 7 and 2), 7.50 (1H, dt, J 8 and 1), 7.57–7.60 (2H, m), 7.61–7.72 (4H, m), 7.78–7.84 (3H, m), 8.61 (1H, dd, J 7 and 1); m/z (ES$^+$) 328 (M$^+$+H).

What is claimed is:

1. A compound of formula I, or a salt or prodrug thereof:

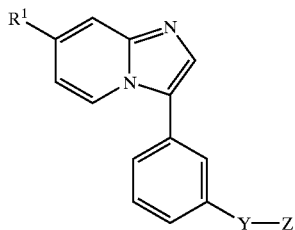

(I)

wherein

Y represents a chemical bond, an oxygen atom, or a —NH-linkage;

Z represents an optionally substituted aryl or heteroaryl group;

$R^1$ represents hydrogen, hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, —CONR$^a$R$^b$ or —CR$^a$=NOR$^b$; and $R^a$ and $R^b$ independently represent hydrogen, hydrocarbon or a heterocyclic group.

2. A compound as claimed in claim 1 represented by formula IIA, and salts and prodrugs thereof:

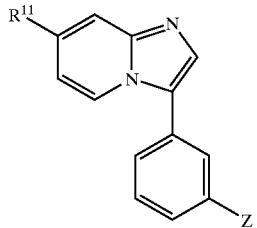

(IIA)

wherein

Z is as defined in claim 1;

$R^{11}$ represents C$_{1-6}$ alkyl, halo(C$_{1-6}$)alkyl, dihalo(C$_{1-6}$)alkyl, hydroxy(C$_{1-6}$)alkyl, heteroaryl, halogen, cyano, trifluoromethyl, C$_{1-6}$ alkoxy, formyl, C$_{2-6}$ alkylcarbonyl, C$_{2-6}$ alkoxycarbonyl or —CR$^4$=NOR$^5$;

$R^4$ represents hydrogen or C$_{1-6}$ alkyl; and $R^5$ represents hydrogen, C$_{1-6}$ alkyl, hydroxy(C$_{1-6}$)alkyl or di(C$_{1-6}$)alkylamino(C$_{1-6}$)alkyl.

3. A compound as claimed in claim 2 represented by formula IIB, and salts and prodrugs thereof:

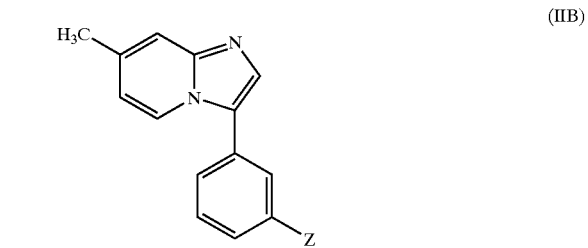

(IIB)

wherein Z is as defined in claim 1.

4. A compound as claimed in claim 2 represented by formula IIC, and salts and prodrugs thereof:

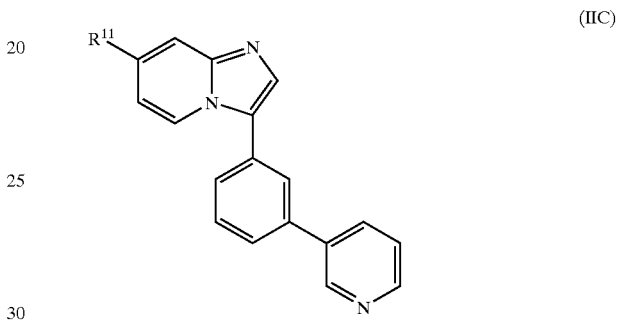

(IIC)

wherein $R^{11}$ is as defined in claim 2.

5. A compound as claimed in claim 2 represented by formula IID, and salts and prodrugs thereof:

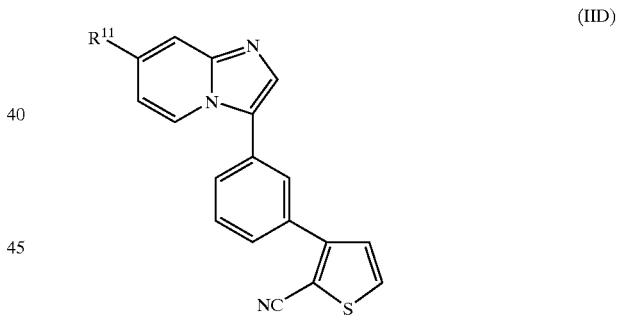

(IID)

wherein $R^{11}$ is as defined in claim 2.

6. A compound as claimed in claim 2 represented by formula IIE, and salts and prodrugs thereof:

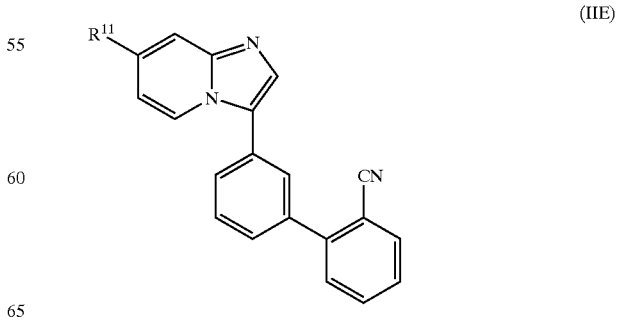

(IIE)

wherein $R^{11}$ is as defined in claim 2.

7. A compound selected from:

3-[3-(7-methylimidazo[1,2-α]pyridin-3-yl)phenyl]thiophene-2-carbonitrile;
3-[3-(7-methylimidazo[1,2-α]pyridin-3-yl)phenyl]thiophene-2-carboxaldehyde;
3-[3-(7-methylimidazo[1,2-α]pyridin-3-yl)phenyl]thiophene-2-carboxylic acid methyl ester;
5-[3-(7-methylimidazo[1,2-α]pyridin-3-yl)phenyl]thiophene-2-carboxaldehyde oxime;
7-methyl-3-[3-(thiazol-4-yl)phenyl]imidazo[1,2-α]pyridine;
7-methyl-3-[3-(thiazol-2-yl)phenyl]imidazo[1,2-α]pyridine;
7-methyl-3-[3-(pyridin-4-yl)phenyl]imidazo[1,2-α]pyridine;
6-chloro-4-[3-(7-methylimidazo[1,2α]pyridin-3-yl)phenyl]pyridin-3-ylamine;
7-methyl-3-[3-(pyridin-2-yloxy)phenyl]imidazo[1,2-α]pyridine;
N-[3-(7-methylimidazo[1,2-α]pyridin-3-yl)phenyl]-N-(2-nitrophenyl)amine;
3-[3-(pyridin-3-yl)phenyl]imidazo[1,2-α]pyridine-7-carboxylic acid methyl ester;
3-[3-(pyridin-3-yl)phenyl]imidazo[1,2-α]pyridine-7-ylmethanol;
3-[3-(pyridin-3-yl)phenyl]imidazo[1,2-α]pyridine-7-carboxaldehyde;
3-[3-(pyridin-3-yl)phenyl]imidazo[1,2-α]pyridine-7-carboxaldehyde oxime;
3-[3-(pyridin-3-yl)phenyl]imidazo[1,2-α]pyridine-7-carboxaldehyde O-(2-hydroxyethyl)oxime;
3-[3-(pyridin-3-yl)phenyl]imidazo[1,2-α]pyridine-7-carboxaldehyde O-(2-dimethylaminoethyl)oxime;
1-[3-(3-(pyridin-3-yl)phenyl)imidazo[1,2-α]pyridin-7-yl]ethanol;
1-[3-(3-(pyridin-3-yl)phenyl)imidazo[1,2-α]pyridin-7-yl]ethanone;
1-[3-(3-(pyridin-3-yl)phenyl)imidazo[1,2-α]pyridin-7-yl]ethanone oxime;
7-chloro-3-[3-(pyridin-3-yl)phenyl]imidazo[1,2-α]pyridine;
7-(furan-3-yl)-3-[3-(pyridin-3-yl)phenyl]imidazo[1,2-α]pyridine;
7-methoxy-3-[3-(pyridin-3-yl)phenyl]imidazo[1,2-α]pyridine;
and salts and prodrugs thereof.

8. A compound selected from:

3'-(7-methylimidazo[1,2-α]pyridin-3-yl)biphenyl-2-carbonitrile;
3-[3-(7-methylimidazo[1,2-α]pyridin-3-yl)phenyl]thiophene-2-carboxamide;
3-[3-(2-cyanothien-3-yl)phenyl]imidazo[1,2-α]pyridine-7-carboxylic acid methyl ester;
3-[3-(7-formylimidazo[1,2-α]pyridin-3-yl)phenyl]thiophene-2-carbonitrile;
3-[3-(7-hydroxyiminomethylimidazo[1,2-α]pyridin-3-yl)phenyl]thiophene-2-carbonitrile;
3-[3-(7-(2-hydroxyethoxy)iminomethylimidazo[1,2-α]-pyridine-3-yl)phenyl]thiophene-2-carbonitrile;
3-[3-(7-(2-dimethylaminoethoxy)iminomethylimidazo[1,2-α]pyridin-3-yl)phenyl]thiophene-2-carbonitrile;
3'-(7-formylimidazo[1,2-α]pyridin-3-yl)biphenyl-2-carbonitrile;
3'-(7-hydroxyiminomethylimidazo[1,2-α]pyridin-3-yl)biphenyl-2-carbonitrile;
3'-(7-difluoromethylimidazo[1,2-α]pyridin-3-yl)biphenyl-2-carbonitrile;
3'-(7-hydroxymethylimidazo[1,2-α]pyridin-3-yl)biphenyl-2-carbonitrile;
3'-(7-fluoromethylimidazo[1,2-α]pyridin-3-yl)biphenyl-2-carbonitrile;

and salts and prodrugs thereof.

9. A pharmaceutical composition comprising a compound of formula I as defined in claim 1 or a pharmaceutically acceptable salt thereof or a prodrug thereof in association with a pharmaceutically acceptable carrier.

10. A process for the preparation of a compound of formula I as defined in claim 1, which comprises:

(A) reacting a compound of formula III with a compound of formula IV:

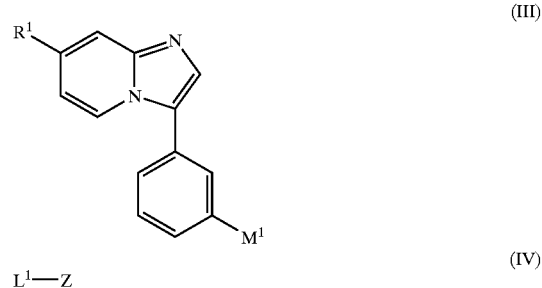

wherein Z and $R^1$ are as defined in claim 1, $L^1$ represents a suitable leaving group, and $M^1$ represents a boronic acid moiety —$B(OH)_2$ or a cyclic ester thereof formed with an organic diol; in the presence of a transition metal catalyst; or (B) reacting a compound of formula IV as defined above with a compound of formula V:

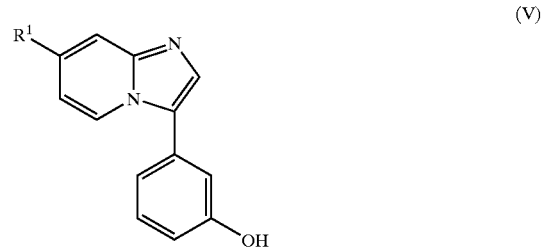

wherein $R^1$ is as defined in claim 1; or (C) reacting a compound of formula IV as defined above with a compound of formula VI:

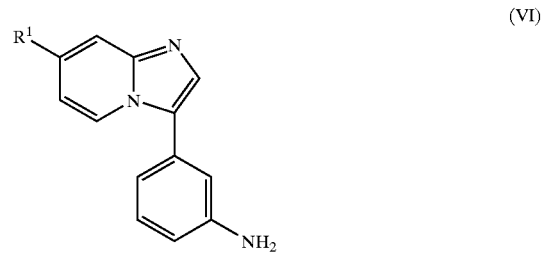

wherein $R^1$ is as defined in claim 1; or (D) reacting a compound of formula IX:

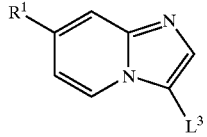

wherein $R^1$ is as defined in claim 1, and $L^3$ represents a suitable leaving group; with a compound of formula XI:

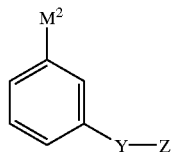

wherein Y and Z are as defined in claim 1, and $M^2$ represents $Sn(Alk)_3$ in which Alk represents $C_{1-6}$ alkyl, or $M^2$ represents a boronic acid moiety $—B(OH)_2$ or a cyclic ester thereof formed with an organic diol, in the presence of a transition metal catalyst; or (E) reacting a compound of formula XIV with a compound of formula XV:

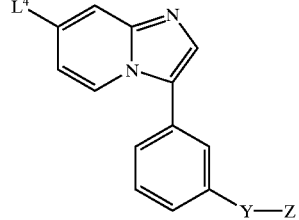

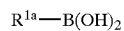

wherein Y and Z are as defined in claim 1, $R^{1a}$ represents an aryl or heteroaryl moiety, and $L^4$ represents a suitable leaving group; in the presence of a transition metal catalyst; and (F) subsequently, if desired, converting a compound of formula I initially obtained into a further compound of formula I by methods known per se.

11. A method for the treatment and/or prevention of anxiety which comprises administering to a patient in need of such treatment an effective amount of a compound of formula I as defined in claim 1 or a pharmaceutically acceptable salt thereof or a prodrug thereof.

* * * * *